United States Patent
Borsic

(10) Patent No.: US 11,419,660 B2
(45) Date of Patent: Aug. 23, 2022

(54) SYSTEM AND METHODS FOR ABLATION TREATMENT OF TISSUE

(71) Applicant: Andrea Borsic, Turin (IT)

(72) Inventor: Andrea Borsic, Turin (IT)

(73) Assignee: Andrea Borsic, Turin (IT)

( * ) Notice: Subject to any disclaimer, the term of this patent is extended or adjusted under 35 U.S.C. 154(b) by 912 days.

(21) Appl. No.: 15/427,884

(22) Filed: Feb. 8, 2017

(65) Prior Publication Data
US 2017/0224402 A1 Aug. 10, 2017

Related U.S. Application Data

(60) Provisional application No. 62/293,102, filed on Feb. 9, 2016.

(51) Int. Cl.
*A61B 18/12* (2006.01)
*A61B 34/00* (2016.01)
(Continued)

(52) U.S. Cl.
CPC ...... *A61B 18/1206* (2013.01); *A61B 18/1815* (2013.01); *A61B 34/25* (2016.02); *A61B 90/37* (2016.02); *A61B 18/1482* (2013.01); *A61B 2018/00577* (2013.01); *A61B 2018/00613* (2013.01); *A61B 2018/00785* (2013.01); *A61B 2018/00791* (2013.01); *A61B 2018/00875* (2013.01); *A61B 2018/1253* (2013.01); *A61B 2018/1432* (2013.01); *A61B 2018/1467* (2013.01); *A61B 2018/1861* (2013.01); *A61B 2034/2065* (2016.02);
(Continued)

(58) Field of Classification Search
CPC ..... A61B 18/1206; A61B 34/25; A61B 90/37; A61B 90/374; A61B 90/376; A61B 90/3762; A61B 18/1815; A61B 2018/00577
USPC .......................................... 600/411, 427, 439
See application file for complete search history.

(56) References Cited

U.S. PATENT DOCUMENTS

2009/0171203 A1* 7/2009 Avital ................... A61B 90/11
600/439
2011/0251607 A1* 10/2011 Kruecker ........... A61B 18/1206
606/34
(Continued)

*Primary Examiner* — Christopher R Harmon
(74) *Attorney, Agent, or Firm* — Caldwell Intellectual Property Law

(57) ABSTRACT

This invention pertains a system and methods for ablation treatment of tissues. The invention aims to aid healthcare professionals in completely treating all the target tissues by fusing computer generated information highlighting which tissues have been treated and which not to images of the tissues. The systems and methods integrate seamlessly with current image-guided procedures and do not require tracking systems to gather the position of the ablation device, as the positon and orientation of the device are identified from images. The invention aims also to improve estimates of the ablation volumes associated to an ablation device by identifying from images the true geometry of devices that might deform during the deployment in tissues; the invention aims to improve estimates of the ablation volumes by using information about the ablation process and about the status of tissues which can be collected from the control system of the ablation device.

14 Claims, 21 Drawing Sheets

(51) Int. Cl.
    *A61B 90/00*         (2016.01)
    *A61B 18/18*         (2006.01)
    *A61B 18/00*         (2006.01)
    *A61B 18/14*         (2006.01)
    *A61B 34/20*         (2016.01)

(52) U.S. Cl.
    CPC ... *A61B 2090/374* (2016.02); *A61B 2090/378* (2016.02); *A61B 2090/3762* (2016.02)

(56) References Cited

U.S. PATENT DOCUMENTS

| | | | |
|---|---|---|---|
| 2012/0173217 A1* | 7/2012 | Heimbecher | A61B 34/20 703/11 |
| 2012/0277763 A1* | 11/2012 | Greenblatt | A61B 34/10 606/130 |
| 2014/0058387 A1* | 2/2014 | Kruecker | A61B 18/148 606/41 |
| 2014/0343404 A1* | 11/2014 | Razzaque | A61B 8/0841 600/424 |
| 2015/0057646 A1* | 2/2015 | Aljuri | A61B 18/04 606/10 |
| 2015/0374260 A1* | 12/2015 | Govari | A61B 5/066 600/417 |
| 2017/0209218 A1* | 7/2017 | Sahay | A61B 6/5235 |
| 2018/0042679 A1* | 2/2018 | Dalal | A61B 18/12 |
| 2018/0161097 A1* | 6/2018 | Zoabi | G06T 17/00 |
| 2020/0214768 A1* | 7/2020 | Baumann | A61B 17/3403 |

* cited by examiner

SYSTEM AND METHODS FOR ABLATION TREATMENT OF TISSUE

RELATED APPLICATIONS

This application claims the benefit of U.S. Provisional Application No. 62/293,102, filed on Feb. 9, 2016.

STATEMENT REGARDING FEDERALLY SPONSORED RESEARCH OR DEVELOPMENT

The research activity leading to this patent application had been partially supported by the SBIR Phase I grant 1R43CA189515-01 awarded from the U.S. National Cancer Institute.

FIELD OF THE INVENTION

The present disclosure pertains generally to systems and methods for interventional guidance of tissue ablation procedures.

BACKGROUND OF THE INVENTION AND RELATED ART

Ablation technologies are used to necrotize tissues for therapeutic purposes. An example of application is treatment of cancer, where ablation is used to treat malignant tissues in order to cure or manage the disease. Another example of application is treatment of arrhythmia, where ablation is used to scar or destroy tissues in the heart that trigger or sustain abnormal heart rhythms.

Various ablation technologies exist, based on different physical principles. Radio Frequency Ablation (RFA) is based on the application of Radio Frequency (RF) energy to the tissues by means of one or multiple contacting electrodes, and on heating up tissues to a temperature high enough to cause tissue necrosis. Microwave Ablation (MWA) is based on the application of Micro Wave (MW) energy to the tissues by means of a contacting antenna, and on heating up tissues to a temperature high enough to cause tissue necrosis. Cryoablation (CRA) is based on the application of cold temperatures to the tissues, by means of a contacting device, and on cooling down tissues to temperatures that cause tissue necrosis. Irreversible Electroporation (IRE) is based on the application to tissues by contacting electrodes of short-duration high-voltage electric Direct Current (DC) pulses which result in damage to tissue cells and in tissue necrosis.

The above ablation techniques can be applied in minimally invasive fashion. RFA, for example, which is used for treatment of liver, lung, breast and other forms of cancer, can be performed percutaneously, with needle-shaped electrodes, which are inserted into the tissues through the skin. RFA is also used, for example, in the treatment of arrhythmia, where heart tissues causing arrhythmia are treated with a catheter carrying an RFA electrode. Similarly MWA can be performed percutaneously, for example, in the treatment of liver cancer and other forms of cancer, using needle shaped MWA antennas. MWA can also be used, for example, in the treatment of arrhythmia, reaching the target tissues with a catheter. Similarly to RFA and MWA, CRA is used percutaneously for the treatment of tumors, by inserting needle-shaped cryo-probes into the tissues, and, for example, in the treatment of heart arrhythmia, by using catheters able to cool down contacting tissues. IRE is used to percutaneously treat tumors by inserting two or more needle-shaped electrodes in the tissues and by applying electric pulses between pairs of them.

In the following the term "ablation device" is used to refer devices able to perform the ablation of tissues, such as, but not limited to, RFA electrodes, MWA antennas, IRE needles, and CRA cryo-probes.

In the minimally invasive use of ablation technologies, the operator has no direct view of the tissues that are being treated, as the ablation device is inserted into the body, for example, percutaneously or endoscopically. These procedures are image-guided, where Computed Tomography (CT), Ultrasound (US), Magnetic Resonance Imaging (MRI), or Fluoroscopy (FL) images are acquired intraoperatively and used to visualize the tissues and the position of the device within the body.

The aim of a procedure is to treat completely the volume of target tissues (e.g. a tumor) and optionally some margins around the target, which are also considered as targets for the procedure. A procedure is adequate if all the target tissues and any defined margin are treated. Reaching adequacy might require multiple overlapping ablations in order to fully treat the volume of target tissues and margins.

In often cases the evaluation of adequacy under image guidance is difficult, as the imaging modality might not be sensitive enough to highlight clearly all the tissues that have been treated, or because the imaging modality might require administration of contrast to the patient for the treated tissues to enhance, but the operator might be limited in the dose of contrast administered, as the contrast might be toxic.

Under image guidance it might be challenging therefore to evaluate whether adequacy has been reached. For example, local recurrence of tumors treated by ablation is largely attributed to procedures that were inadequate, but interpreted as adequate, resulting in certain malignant tissues left untreated.

Systems have been proposed to improve chances of fully treating target tissues and reaching adequacy. Many of the proposed systems integrate a treatment planning system with a navigation system. The treatment planning system allows the operator to develop an interventional plan based on a number of positions and orientations of the ablation device that will result in the complete treatment of the target tissues—through the set of treatment volumes deriving from the different positions and orientations of the device. During the execution of the plan, the navigation component will acquire the intracorporeal position and orientation of the ablation device and provide some form of feedback, usually through a Graphical User Interface (GUI), to the operator to facilitate placing the ablation device in the positions and orientations required by the treatment plan. Examples of such systems are in patents US 2011/0251607 A1, U.S. Pat. No. 7,452,357 B2, US 20130317363 A1.

Systems that include a navigation component relay usually on optical, electromagnetic, or ultrasound surgical tools tracking technologies to track the spatial position and orientation of the ablation device. These tracking systems increase the cost of the overall ablation system, introduce clutter in the operating room, in certain cases limit the movement of the operator—optical systems require the line of sight to the surgical tool to be uninterrupted—and require integration of the ablation device with the tracking technology, by securing, for example, fiducials, optical markers, or electromagnetic coils to the ablation device.

SUMMARY OF THE DISCLOSURE

The disclosed invention is directed to a system and methods for conducting tissue ablation that integrate seamlessly with current non-navigated image guided ablation approaches, and does not require to develop or follow treatment plans, but is based on simply highlighting on patient's images, which target tissues have been treated and which target tissues still require treatment, rendering the evaluation of adequacy a visual and straightforward task.

Highlighting of treated and untreated target tissues is based on defining a volume of target tissues at the start of the procedure and on progressively building a map of treated tissues. Difference between the volume of target tissues and of treated tissues, as from the map of treated tissues, allows to define which tissues still need treatment.

The map of treated tissues is built by progressively accumulating the effects of the single ablations that are performed during the procedure. To this end the system needs to estimate the volume of each single ablation and the intracorporeal position of the ablation device, so that the correct tissues in the map can be marked as treated. If at any stage of the procedure images that show which tissues have been treated are available, for example because contrast has been administered, the volume of treated tissues available from the image is accumulated in the treated tissues map as well.

The position and orientation of the ablation device, which are required to build the map of treated tissues, are estimated solely from the images, with image analysis algorithms, not requiring therefore the presence of surgical tool tracking technologies.

Expressions of embodiments of the invention provide a system (claim 1) and a method (claim 10) for treating tissue in a body volume with an ablation device. This system and method are not based on the definition and execution of a treatment plan, but simply on highlighting on the patient images, in a Graphical User Interface (GUI), the target tissues that have been treated, or the target tissues that are yet to be treated, or both, depending on the operator's preference, aiding in this way the evaluation of adequacy. The enhanced views offered by the system, consisting in medical images and computer generated highlights, renders adequacy evaluation a visual and immediate task. The system builds a treated tissues map by progressively accumulating in the map the volumes of tissues treated by each single ablation of the procedure. The map is used to determine which target tissues have been treated and which not at any stage of the procedure, allowing highlighting of such tissues. The map is built by considering the ablation volume of the ablation device and the intracorporeal position and orientation of the ablation device. The system acquires the position and orientation of the ablation device by identifying them from images, therefore not requiring a surgical tool tracking technology.

Further, the invention aims at improving the estimation of the ablation volume of a device (claim 16) which consists in recognizing from images the geometry of ablation device, when the device might be subject to deformation when deployed in the tissues. The identified geometry of the deployed device is used to better estimate the ablation volume. This is possible, for example, by using computational models that simulate the physics of the ablation and which are fed with the identified geometry of the device as deployed in tissues. This method applies to any ablation system that needs estimating the ablation volume of an ablation device that might be subject to deformations when deployed (claim 16). An exemplar embodiment of an algorithm able to recognize in CT images the position and orientation of an RFA electrode, and the angle around the shaft of the electrode to which each tine deploys is provided.

Claim 16 claims the benefit of the anteriority date of the provisional patent application U.S. 62/293,102 submitted on Feb. 9, 2016.

Further, the invention aims at improving the estimation of the ablation volume of a device, with a method which consists in reading from the ablation device controller information about the ablation process, like, for example, the level of power applied to the ablation device, and/or information reflecting the status of the tissues, like, for example, the electrical impedance of tissues, which reflects the desiccation, the electromagnetic reflection coefficient, which reflects the desiccation, or the temperature, and using this information to update a computational model used to predict the ablation volume. This method applies to any ablation system that needs estimating the ablation volume of an ablation device (claim 17).

DETAILED DESCRIPTION

Exemplary embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The exemplary embodiments of the present disclosure are described with respect to ablative therapy of a human, and some figures show images acquired on animals. It should be understood that the exemplary embodiments can be applied to the body, or portions of the body, whether human or animal.

Figure 1:
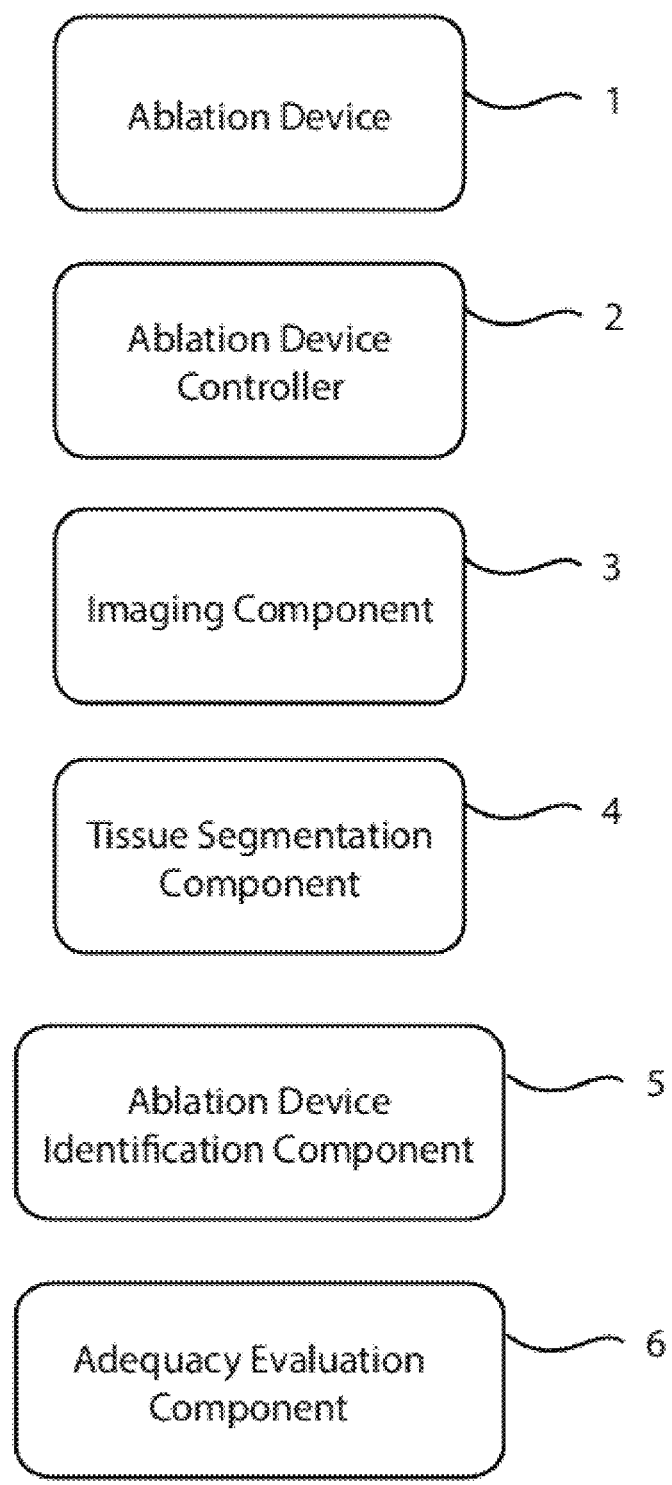
FIG. 1 depicts the system components of an exemplary embodiment of claim 1.

FIG. 1 depicts components of the ablation system object of the present invention.

Figure 2:
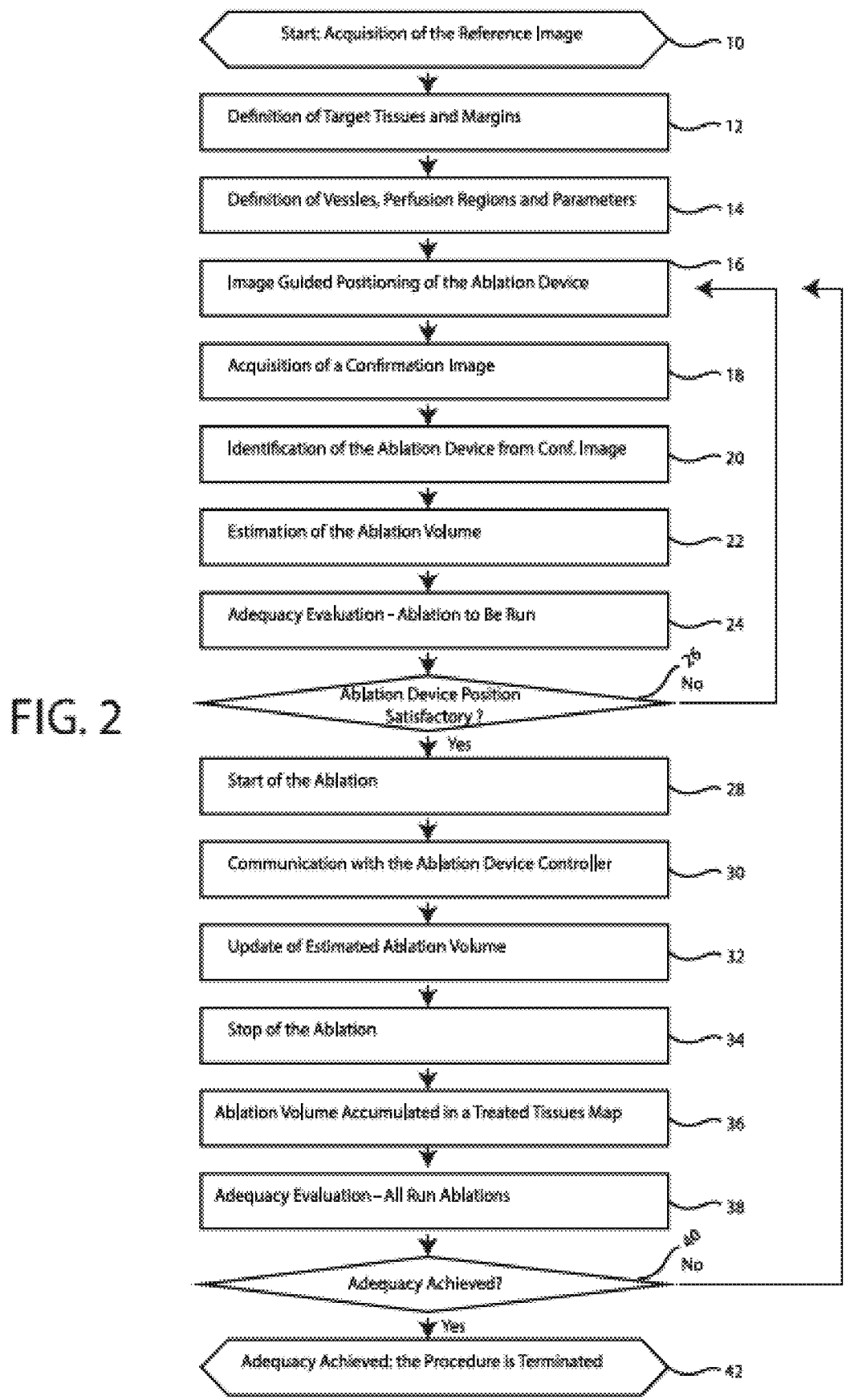
FIG. 2 depicts the flowchart for the operation of the exemplary system of claim 1.

FIG. 2 shows a flowchart representing the operation of the ablation system object of the present invention.

FIG. 1 depicts an overview of the ablation system according to various embodiments of the present disclosure. As shown in FIG. 1 the system includes an ablation device (1); this device can comprise a single or multiple RFA electrodes acting in monopolar or multipolar fashion, a single or multiple MWA antennas, a single or multiple IRE electrodes, a single or multiple cryo-probes, or a single or multiple devices able to ablate tissues thermally or by other means. The system comprises also an ablation device controller (2) which controls the ablation effect of to the ablation device (1) (e.g. by providing RF or microwave energy, by providing electric pulses for IRE, or by providing refrigeration for cryoablation probes). The ablation device controller (2) might optionally collect information that characterizes the tissues, such as the electrical impedance of tissues in RFA, indicative of the level of desiccation of tissues, the electromagnetic reflection coefficient in microwave ablation, indicative of the level of desiccation of tissues, or other information about tissues which might me collected by the ablation probe controlled (2) from sensors mounted on the ablation device (1), like, for example, but not limited to, the temperature of tissues. As shown in FIG. 1 the system includes an imaging component (3) which allows capturing images of the patient, wherein such images can capture also the ablation device (1) as deployed in the tissues. The imaging component (3) can consist, for example, in a CT scanner, a US scanner, an MRI scanner, a FL system, or in other kinds of imaging systems. As shown in FIG. 1 the ablation system includes a tissue segmentation component (4). This component receives images from the imaging component (3) and allows a human operator, through a GUI, to define one three-dimensional image as a reference image. The reference image will be used by the tissue segmentation component (4) to segment different tissues, as described in the following, and subsequent images acquired by the ablation system, through the imaging component (3), will be spatially registered to this reference images, so that features identified in those subsequent images can be spatially referred to the tissues segmented in the reference image. The tissue segmentation component (4) allows the operator to manually, or with semi-automatic, or with automatic algorithms, to segment and define three-dimensionally the ablation target tissues. The tissue segmentation component (4) might additionally offer a functionality to automatically create tissue margins, of an operator specified thickness, around the previously defined target tissues. These tissue margins, if defined, are also a target tissue for the ablation. It is common, for example, in the treatment of cancer, to treat a certain thickness of margins around the tissues that are identified as malignant and that are to be treated.

Figure 19:
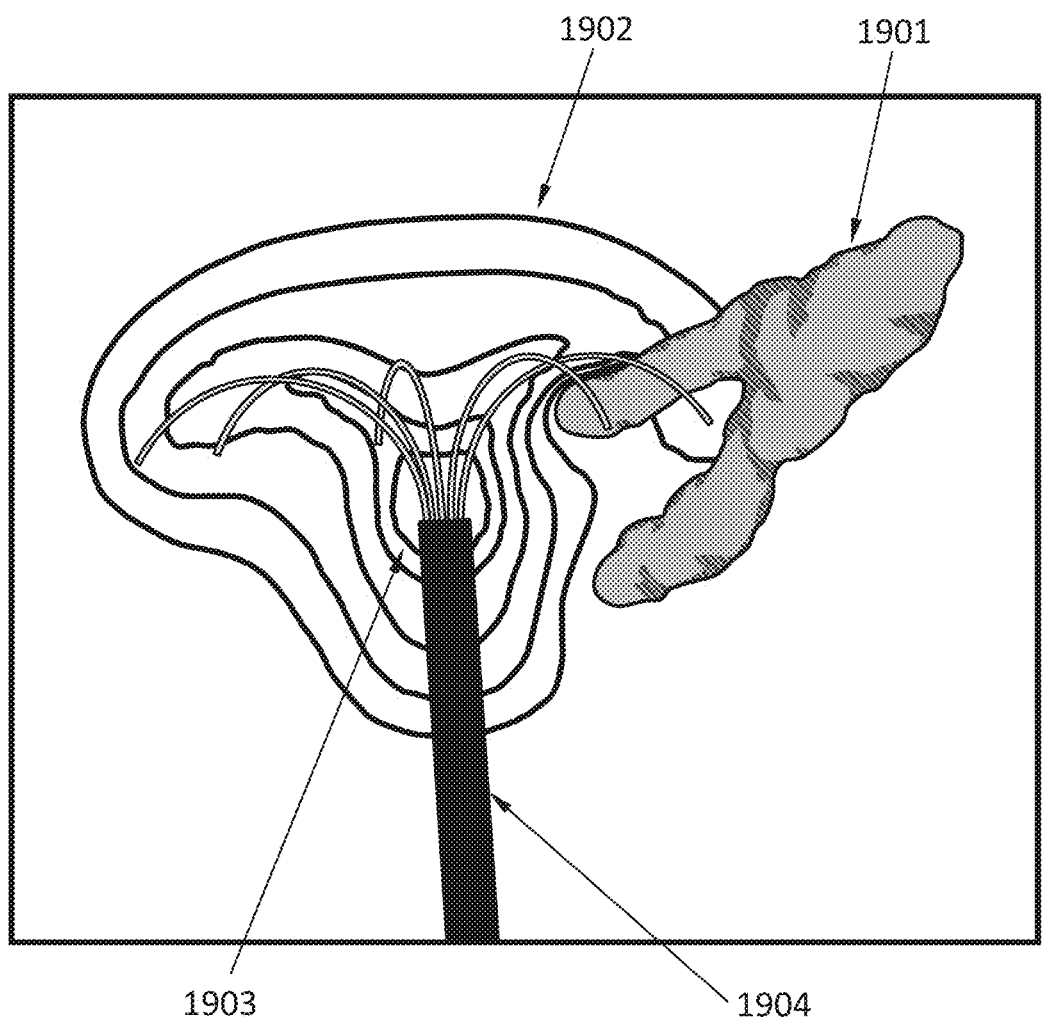
FIG. 19 depicts a CT slice to which have been superimposed an RFA electrode model and temperature isolines demonstrating the heat sink effect of a vessel on the temperature field.

Additionally the tissue segmentation component (4) might offer the functionality to segment three-dimensionally local vasculature. The segmented vasculature will optionally be used by the adequacy evaluation component (6) to account for the heat-sink effect of vessels and more accurately estimate the ablation volume, as discussed later and as illustrated by FIG. 19. Additionally the tissue segmentation component (4) might offer the functionality to segment three-dimensionally different regions of tissues and to specify the perfusion rates for the defined tissue regions. This information will optionally be used by the adequacy evaluation component (6) to more accurately estimate the ablation volume. Perfusion is a phenomenon that removes heat from the ablation site, and higher or lower rates of perfusion result in smaller or larger ablation volumes respectively. Additionally the tissue segmentation component (4) might use images to estimate perfusion rates and regions of tissues with different perfusion rates, as an alternative to user input, or in addition to user input.

The ablation device identification component (5) is a component that uses automatic image processing algorithms, or semi-automatic image processing algorithms, or manual processes, where the operator might provide input through a GUI, to identify the intracorporeal positon and orientation of the ablation device (1) and optionally to identify, for ablation devices that might be subject to deformations, the geometry of the ablation device (1) as deployed in the tissues. The intracorporeal positon and orientation of the ablation device (1), and optionally the identified geometry of the ablation device (1), are fed to the adequacy evaluation component (6) and will be used to build a map of treated tissues as discussed later.

Identifying the position and orientation of the ablation device (1) solely from images is an advantageous embodiment, as other ablation systems are based on surgical tool tracking technologies, where the ablation device position and orientation is tracked by optical, electromagnetic, or ultrasound means using dedicated hardware and software components. The addition of these tracking components to the ablation system is expensive, increases clutter in the operating room, might pose restrictions on the movement of the operator, and requires generally the use of dedicated ablation devices that integrate with the specific tracking technology.

Figure 4:
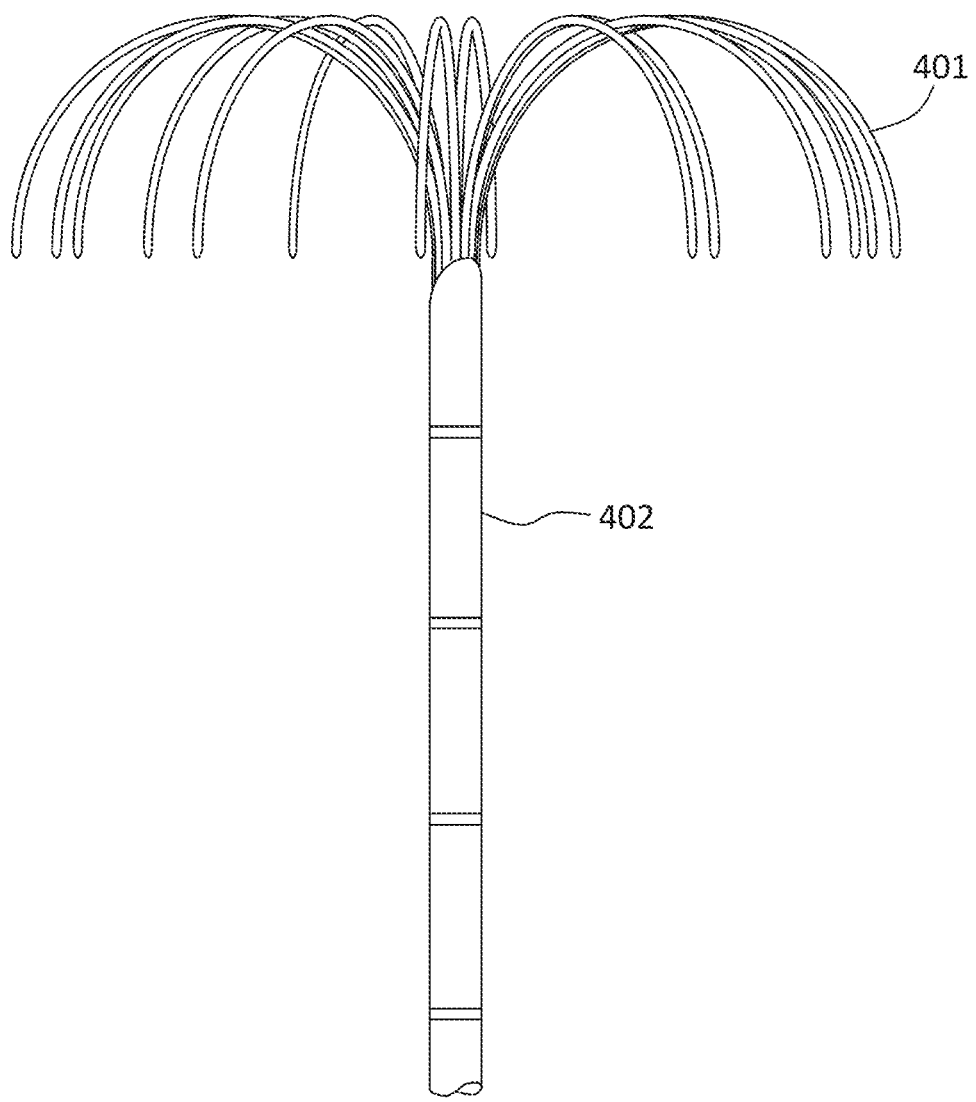
FIG. 4 depicts an example of a common commercial RFA electrode which deploys tines.

Certain ablation devices comprise flexible parts, or otherwise parts that are rigid, but which are mechanically connected by flexible joints. As an example, FIG. 4 shows, as an example, a commercial RFA electrode formed by a hollow shaft (402) which is inserted into the tissues, and by 14 tines, which deploy in an umbrella fashion— (401) indicates one tine. Tines are metallic filaments that are housed inside the shaft during device insertion. Tines are deployed in the tissues after insertion in order to create a larger volume of ablation. Tines are formed by shape-memory metal, and, once deployed, each of them should in principle form the arch of a semi-circle. Tines should also, in principle, deploy with regular angles around the shaft between any two tines. For example, for an electrode with 14 tines the angle around the shaft between any two tines should be 360/14=25.7 degrees. As tines are thin metallic filaments they are subject to deformation when deployed in tissues, and, besides other forms of deformation, the angle around the shaft between any two tines is usually not regular, and can change significantly between different pairs of tines.

These changes in the geometry of the ablation device (1) when deployed in tissues, which are normally not considered, affect the ablation volume of the ablation device (1).

In this advantageous embodiment the ablation device identification component (5) implements functions for identifying the intracorporeal position and orientation of the ablation device (1), and, for ablation devices which might be subject to deformation, functions for identifying the geometry of the ablation device (1) as deployed in the tissues. This identified ablation device (1) geometry will be used by the adequacy evaluation component 6) to update the estimated ablation volume of the ablation device (1), based on the deployed geometry of the ablation device (1).

Figure 3:
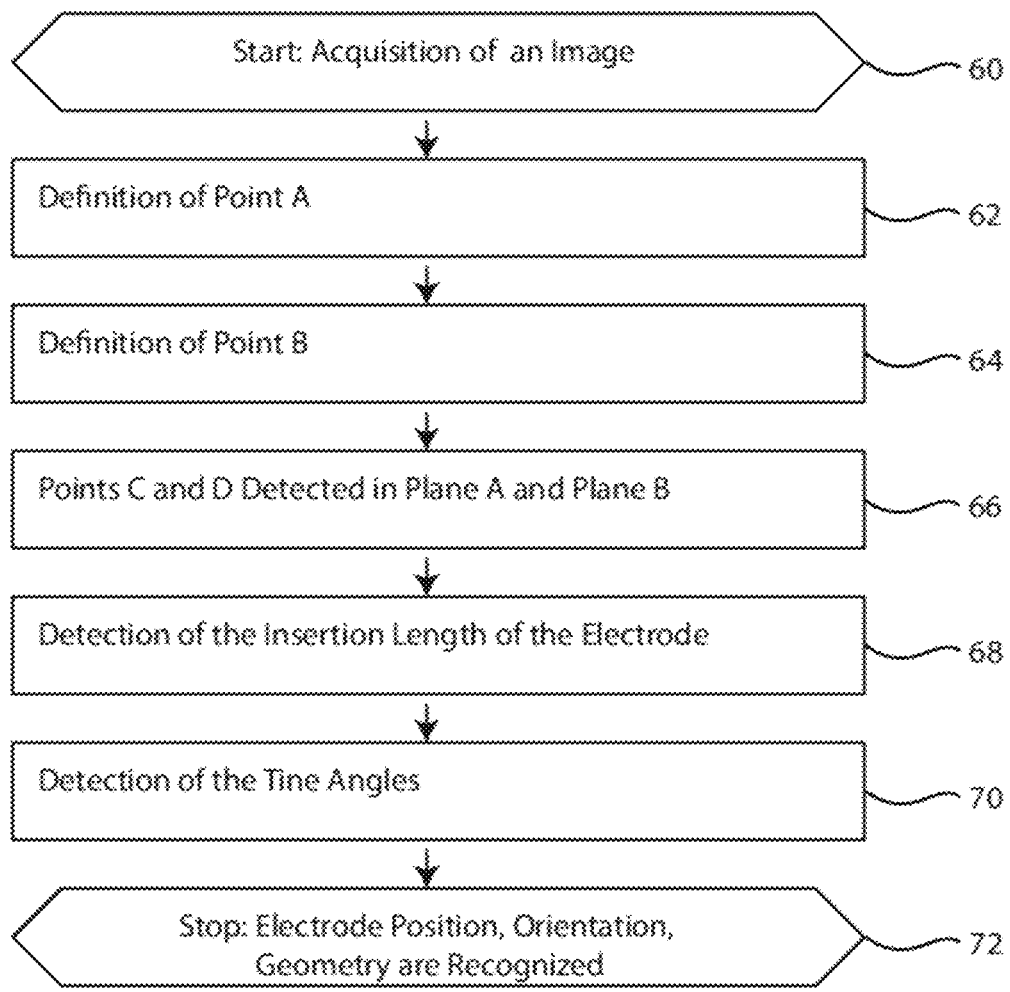
FIG. 3 depicts the flowchart of an exemplary embodiment of an algorithm able to able to recognize in CT images the position and orientation of an RFA electrode, and the angle around the shaft of the electrode to which each tine deploys.

FIG. 3 illustrates a flowchart of an exemplar embodiment of an algorithm for semi-automatically locating RFA electrodes similar in shape to electrode in FIG. 4 and for identifying the angle of deployment around the shaft of each tine of the electrode from analysis of CT images. This embodiment is merely an example of the disclosure and may be embodied in various forms, using different image analysis algorithms and with algorithm designs that are specific to different ablation devices from the ablation device considered in this embodiment; finally this embodiment is demonstrated on CT images acquired on animals, application to humans is identical, and we do not intent to limit by any means the scope of this embodiment, even if disclosed simply for exemplar purposes, to animals.

Figure 5:
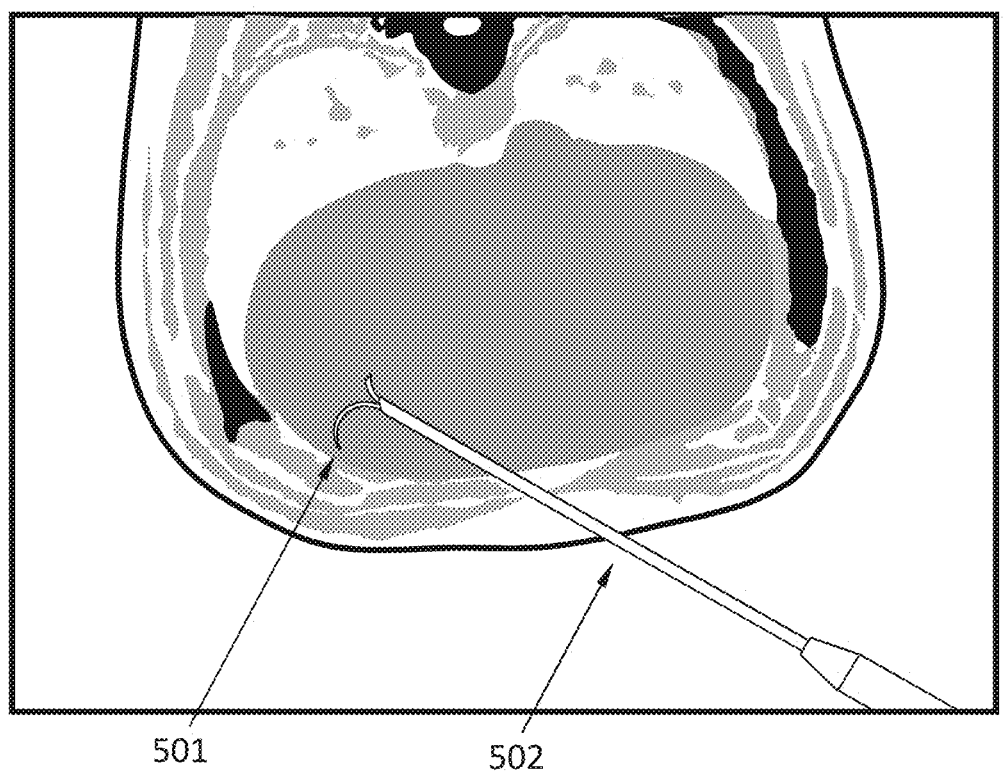
FIG. 5 depicts a CT scan of an RFA electrode deployed in tissues.

FIG. 5 shows a CT image of an RFA electrode with tines deployed in the tissues of an animal. The image is a 2D slice of a 3D CT volume. The slice passes by the shaft of the RFA electrode (501) and intercepts one of the tines (501), which is visible as a semi-arch.

Figure 6:
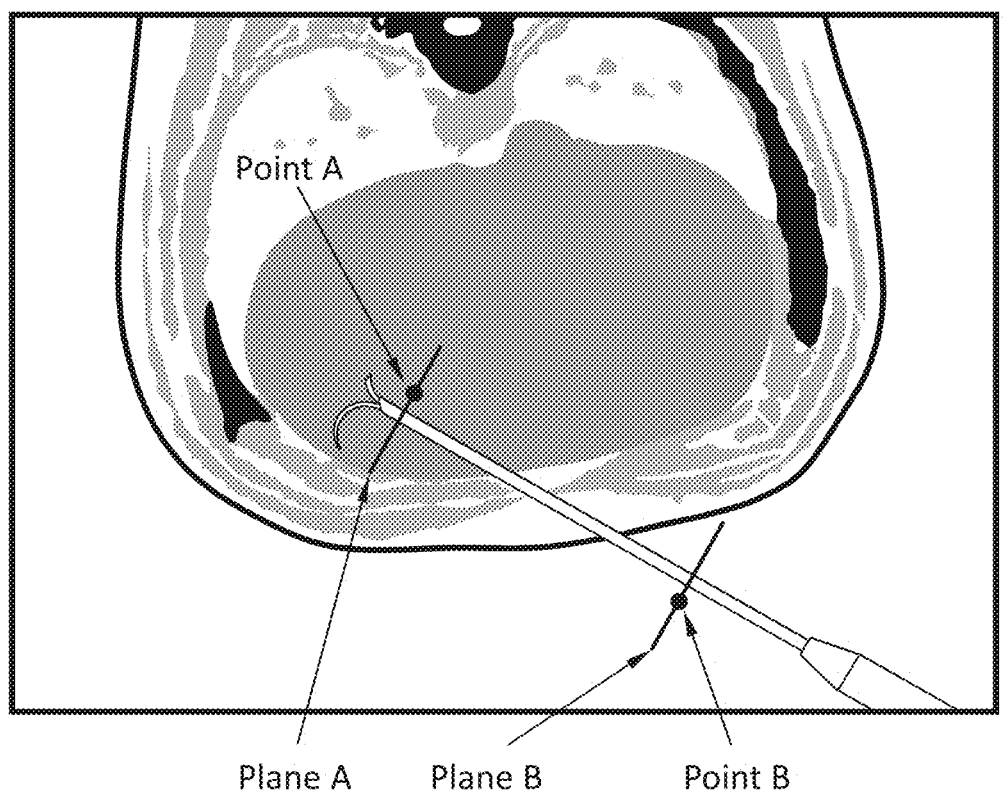
FIG. 6 depicts the CT scan of FIG. 5 where two input points provided by an operator are shown.

Switching to the flowchart of FIG. 3, the electrode identification algorithm starts with the acquisition with the imaging component (3) of an image capturing the RFA electrode deployed in the tissues (step 60). The operator, using a GUI, is shown 2D views of the image and using a GUI and an input device, like, for example a computer mouse or a trackpad, clicks on a point near the distal end of the ablation device (step 62); we label this point as "Point A". FIG. 6 depicts a Point A, which has been rendered as a white circle for illustration purposes. Point A has been depicted proposely off the center of the shaft of the electrode, as the user is required only to click in the proximity of the distal end of the electrode, but not exactly on the electrode. As the position of the 2D slice relative to the 3D image volume is known, this operation defines the 3D coordinates of Point A. Through the same GUI, input device, and method, the operator will click on a 2D slice, which can be different from the previous slice defining point A, near the proximal end of the ablation device (1) defining a "Point B" (step 64) as illustrated in FIG. 6. This operation defines the 3D coordinates of Point B.

Point A and Point B define a line passing by the two points, Line AB, which is an approximation to the axis of the shaft of the electrode, as the operator is required to pick the two points only in the proximity of the shaft, but not on the shaft. The next steps of the electrode identification algorithm aim to identify the exact axis of the RFA electrode shaft.

The electrode identification algorithm computes the Line AB from Point A and Point B. The electrode identification algorithm defines a plane passing by point A, and normal to Line AB, labeled plane A, and a plane passing by point B and normal to Line AB, labelled Plane B. These planes are used for sampling the image intensity. By construction the two planes are likely to intersect the shaft of the electrode in the CT 3D image, as visible in FIG. 6, where the planes are indicated by two white segments. The planes are constructed to have a finite extension, bounding them to, for example, 3 cm respectively from Point A and Point B. Bounding the planes makes them likely to intersect the shaft of the electrode, if the operator picked Point A and Point B not exceedingly far from the shaft of the electrode, and at the same time unlikely to intersect other structures, in the image, that have a high CT intensity as the metallic electrode shaft.

Figure 7:
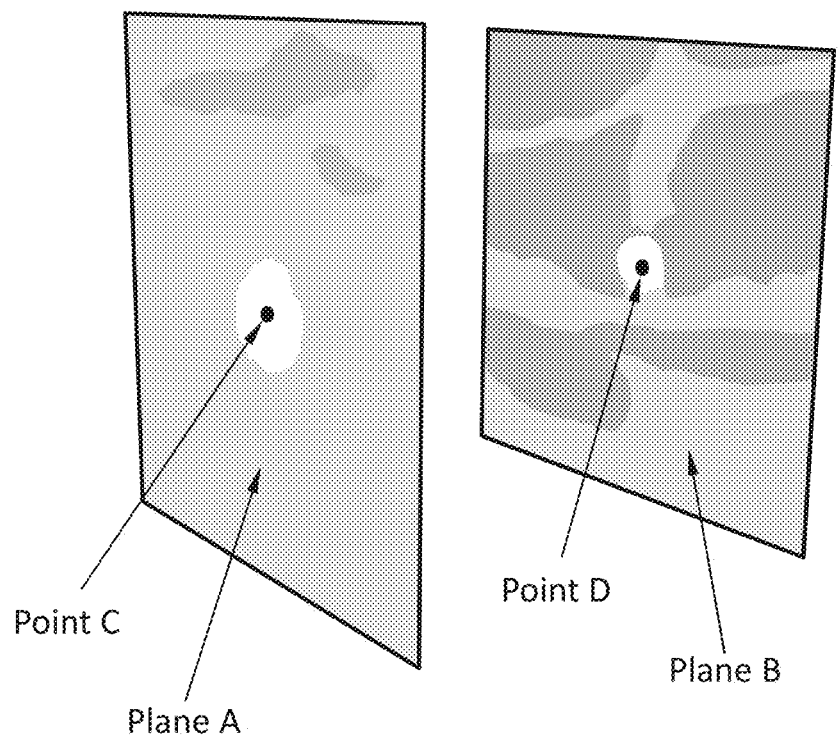
FIG. 7 depicts two sampling planes that are used to sample the intensity values of a CT volume image capturing a deployed RFA electrode.

The CT image values, sampled on Plane A and Plane B, is illustrated in FIG. 7. A high intensity spot result at the location in the planes where the shaft of the electrode is intersected, being the shaft metallic. Locating of the maximum intensity point on plane A defines a Point C in space, which is on or near the center of the electrode shaft, and near the distal end of the electrode. Locating of the maximum intensity point on plane B defines a Point D in space, which is on or near the center of the electrode shaft, and near the proximal end of the electrode, this is step 68 of FIG. 3.

Figure 8:
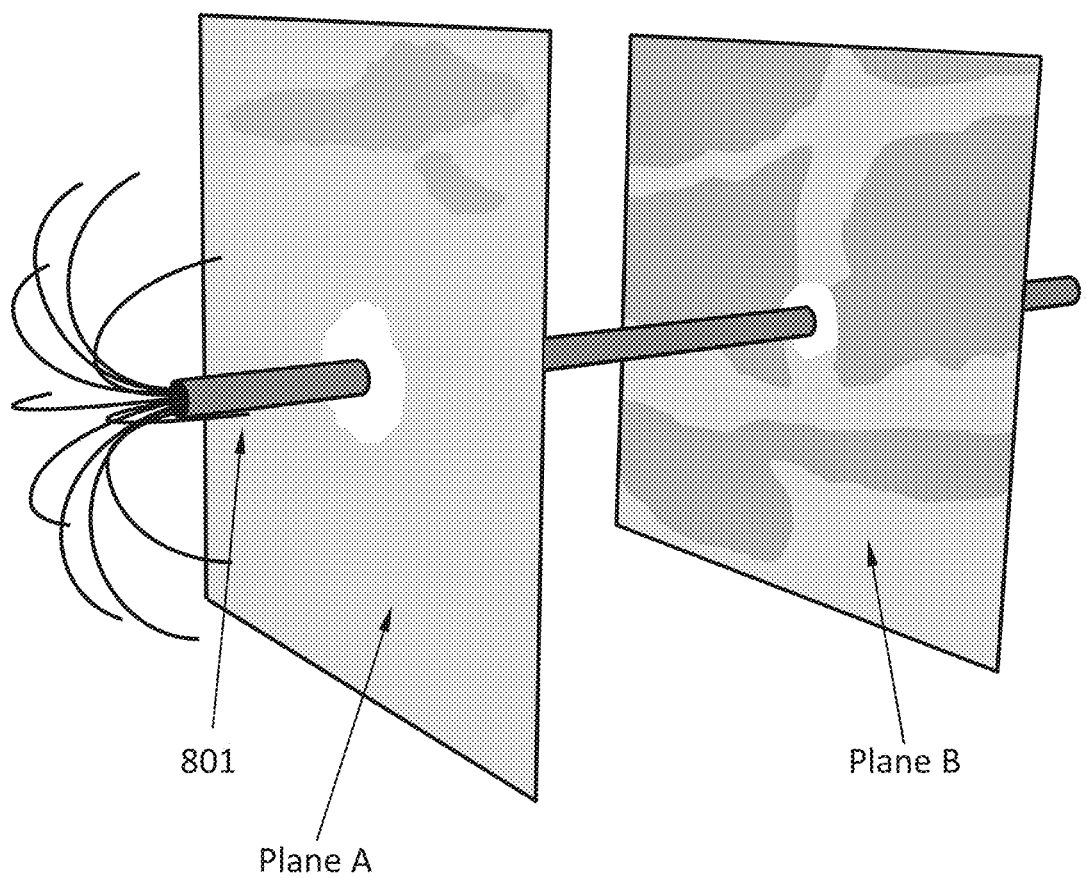
FIG. 8 depicts the two sampling planes of FIG. 7 with the addition of an RFA electrode model to better illustrate the spatial relationship.

The line "Line CD", passing by the points Point C and Point D is therefore a good estimation of the axis of the electrode shaft, as points Point C and Point D have are on the shaft of the electrode. In FIG. 8 a computer model of an RFA electrode (801) has been rendered together with Plane A and Plane B to illustrate spatial relationships. The computer model of the electrode has been built with its shaft passing by Point C and Point D, as the real electrode captured by the CT image.

The preceding algorithm steps have estimated a line, Line CD, representing the axis of the electrode shaft as in the tissues. Additionally to these steps, full determination of the position of the electrode requires determining the position of the electrode along Line CD, or how deep the electrode has been inserted in the body along Line CD. This can be achieved locating, for example, in the image the point along Line CD where the tines attach to the electrode shaft. For this purpose the electrode identification algorithm defines a cylindrical surface over which the intensity of the image is sampled, this allows estimating such point, as discussed next.

Figure 9:
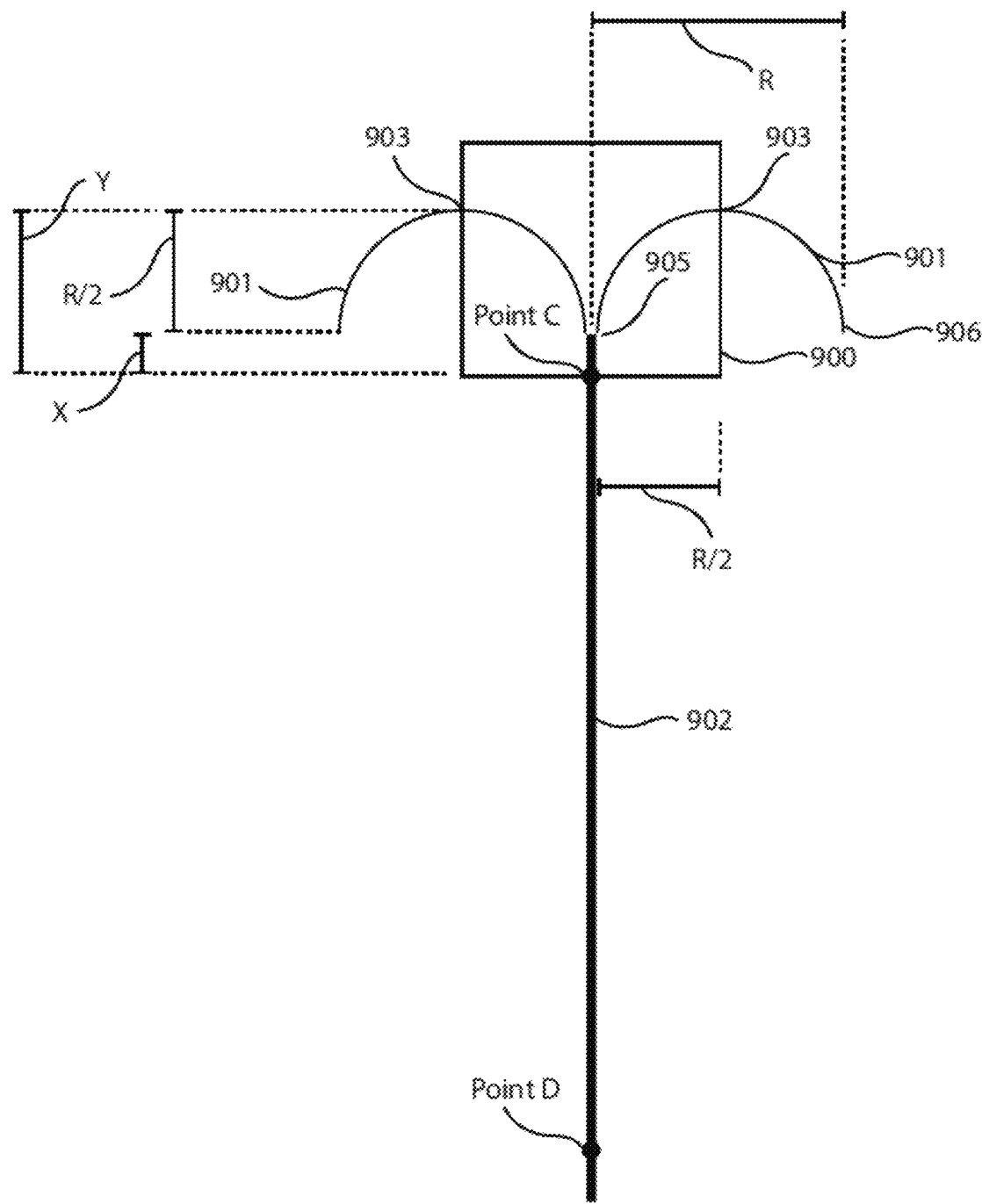
FIG. 9 depicts the geometry of a sampling cylindrical surface used to sample the intensity values of a CT volume image capturing a deployed RFA electrode.

FIG. 9 shows the shaft of the electrode (902), Point C and Point D as identified by the preceding steps and laying on the shaft, two tines (901) of the multiple tines the electrode might have.

The objective of this next step is to determine the offset X, along Line CD, between the point C and the point where the tines attach to the electrode (905). This offset determines the position of the electrode along Line CD, and therefore completely the position and orientation of the electrode, together with Line CD which is known at this point.

The tines (901) of the RFA electrode we consider are assumed to be semi-circles with a distance between the tip of the tine (906) and the point where they connect to the shaft of the electrode (105) of R. The item (900) represents the cylindrical surface used for sampling the image. The cylinder (900) is coaxial with Line CD, has a base that passes by point C and extends vertically for a certain extension, for example R. The requirement is that the height of the sampling cylinder is greater than Y, or X+R/2, so that the cylinder is guaranteed to intersect the tines of the electrode at points 903. Point C is in the proximity of point 105 (the operator is requested to define a Point A in the proximity of the distal end of the electrode, and point C results in the neighborhood of point A) —so a height of the cylinder of R is likely to be sufficient for the tines to intersect the lateral surface of the cylinder at points 903, as in FIG. 9. The radius of the cylinder is defined to be R/2, so that the cylinder will intercept the tines at points 903 that are at the apex of the tines; using a cylinder radius of R/2 determines therefore that the intersection points 903 have an offset from point 905 of R/2 along the Line CD, and that Y=X+R/2.

Figure 10:
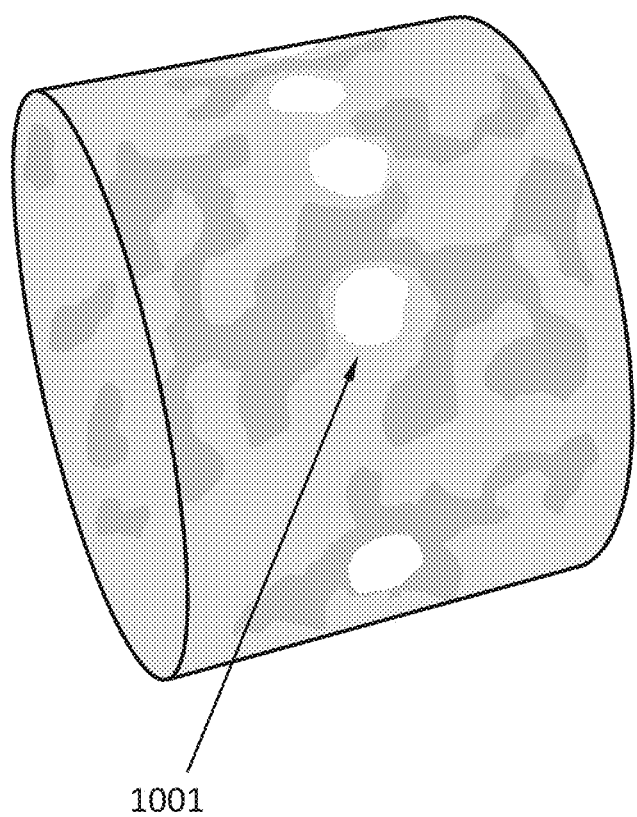
FIG. 10 depicts a sampling cylindrical volume which has been used to sample the intensity values of a CT volume image capturing a deployed RFA electrode.

FIG. 10 shows a sampling cylinder used to sample the CT image in FIG. 6 according to the above procedure. The image intensity values on the surface of the cylinder present local high intensity spots at the points where each tine intersect the lateral surface of the cylinder, as the tines are metallic. One of these intersection spots is labeled (1001) for illustrative purposes. The spots are not evenly spaced around the cylinder, reflecting the uneven deployment of the tines.

Detection of the local maxima of the intensity values over the surface of the cylinder allows determining the longitudinal position of the tines along Line CD, as well as the angular position around the line CD.

The image intensity values sampled on the sampling cylinder (900) can be expressed in cylindrical coordinates (z, 8) where z is a longitudinal coordinate along Line CD, with Point C as origin, and 8 is the angular position around Line CD. This allows representing the sampled values in the plane (z, 8) as in FIG. 11.

As in FIG. 10, intersections of the tines in the image with the sampling cylinder surface, now flattened in the (z, 8) plane, result in bright spots as (1101). Summing the values in the sampled image of FIG. 11 over pixel columns of the image, results in a vector of values which is plotted in FIG. 12, where the intensities (unit of measure Hounsfield Unit, HU) of the single local maxima in FIG. 11 add up, as they are vertically aligned, or close to aligned, giving rise to a single peak value in the vector of sums over pixel columns. The abscissa of the peak in FIG. 12 (1201) reflects the distance, along Line CD, between the point C and the intersection points (903) of FIG. 9, or Y of FIG. 9. This allows determining X as Y−R/2, where R is the radius of the electrode's umbrella of tines, as in FIG. 9. Therefore the position of point 105, where the tines attach to the electrode is completely known. This, together with knowledge of Line CD, determines completely the position and orientation of the electrode in the image.

Figure 13:
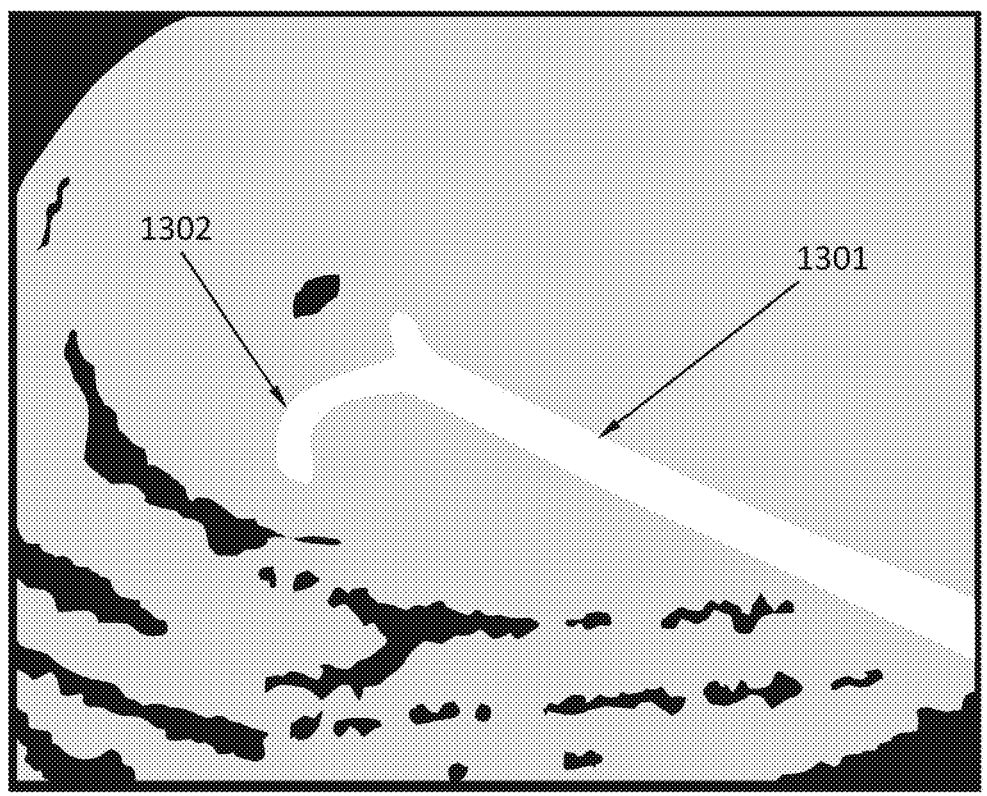
FIG. 13 depicts the detail of a CT image of an RFA electrode deployed in tissues.
Figure 14:
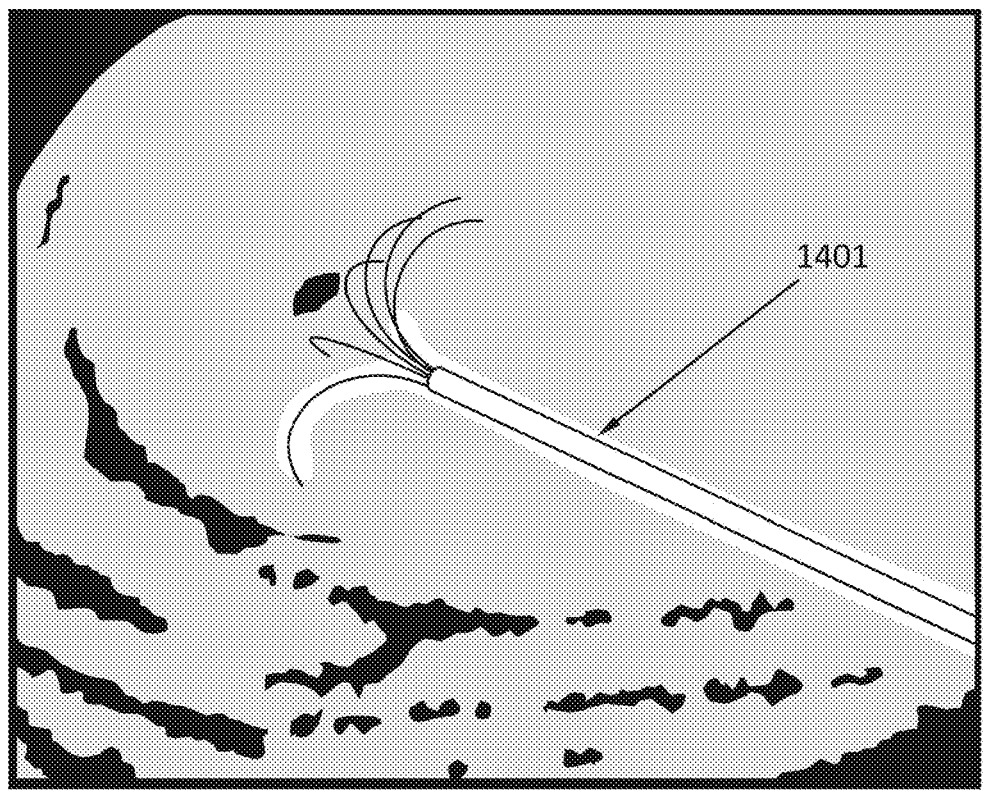
FIG. 14 depicts the CT image of FIG. 13, where of model of an RFA electrode has been rendered at a spatial position and orientation matching those of the true electrode visible in FIG. 13.

FIGS. 13 and 14 demonstrate this above step of the electrode position and orientation identification algorithm, which is labeled as step 68 in the flowchart of FIG. 3. FIG. 13 shows a view of a 2D slice of a 3D CT image of a deployed RFA electrode, where the image slice intercepts the electrode shaft (1301) and one of the tines (1302). The preceding steps of electrode identification algorithm have been applied to the full 3D image to locate the electrode. The resulting known position and orientation of the RFA electrode allow to render in FIG. 14 a computer model of the electrode (1401) correctly positioned in the image, at a location and orientation which coincide with the physical electrode position and orientation.

The next step of the electrode identification algorithm in the flowchart of FIG. 3 is step 70, which aims at detecting the angular position of each tine around the shaft of the electrode, or equivalently around line CD.

Figure 11:
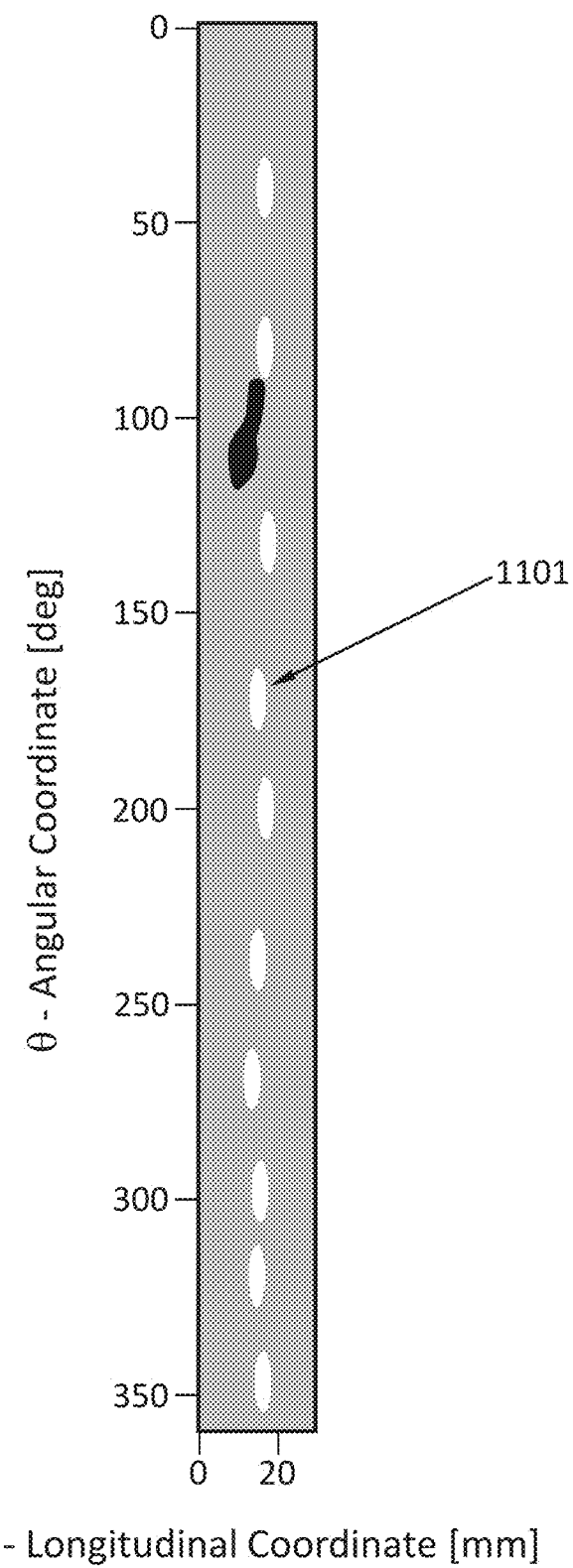
FIG. 11 depicts the CT intensity values sampled on the sampling cylinder of FIG. 10 but represented "flattened" in a plane.
Figure 12:
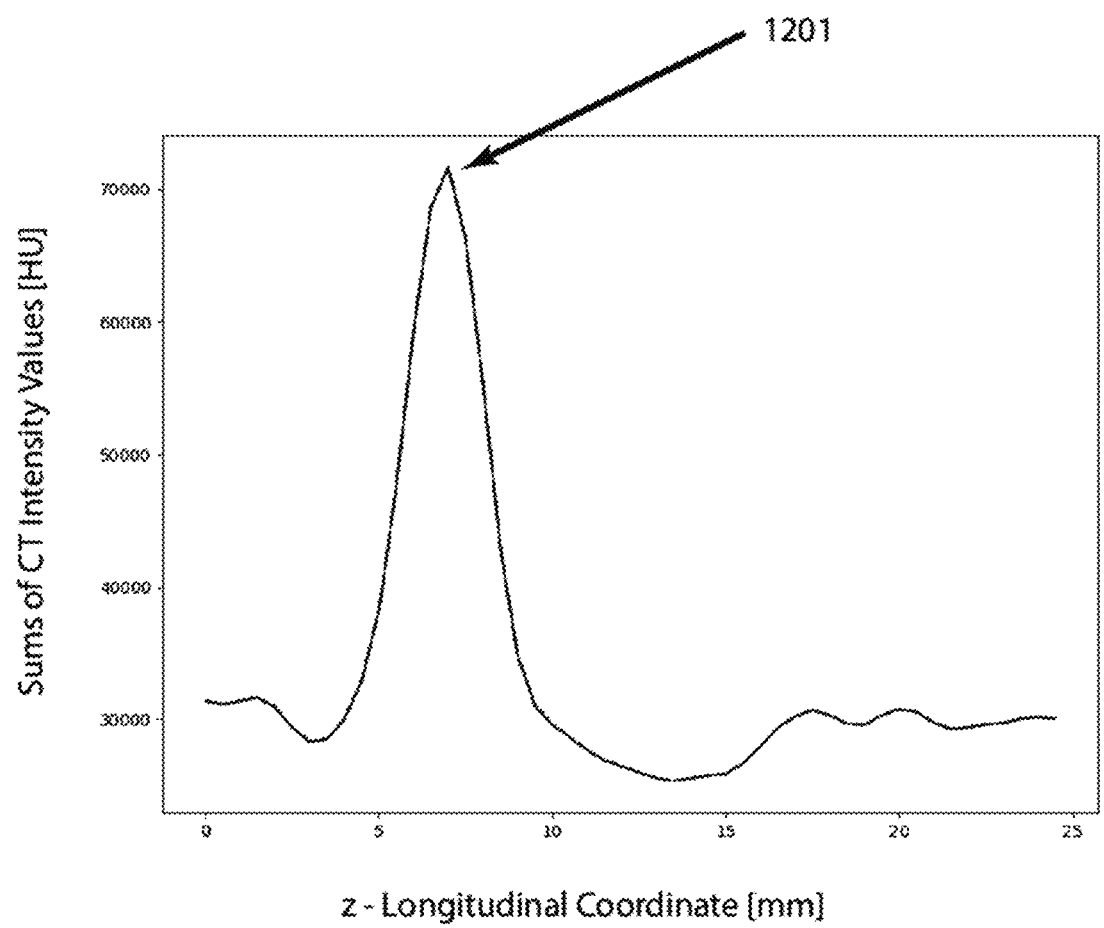
FIG. 12 depicts data values obtained by summing by columns the pixel intensities from FIG. 11.
Figure 15:
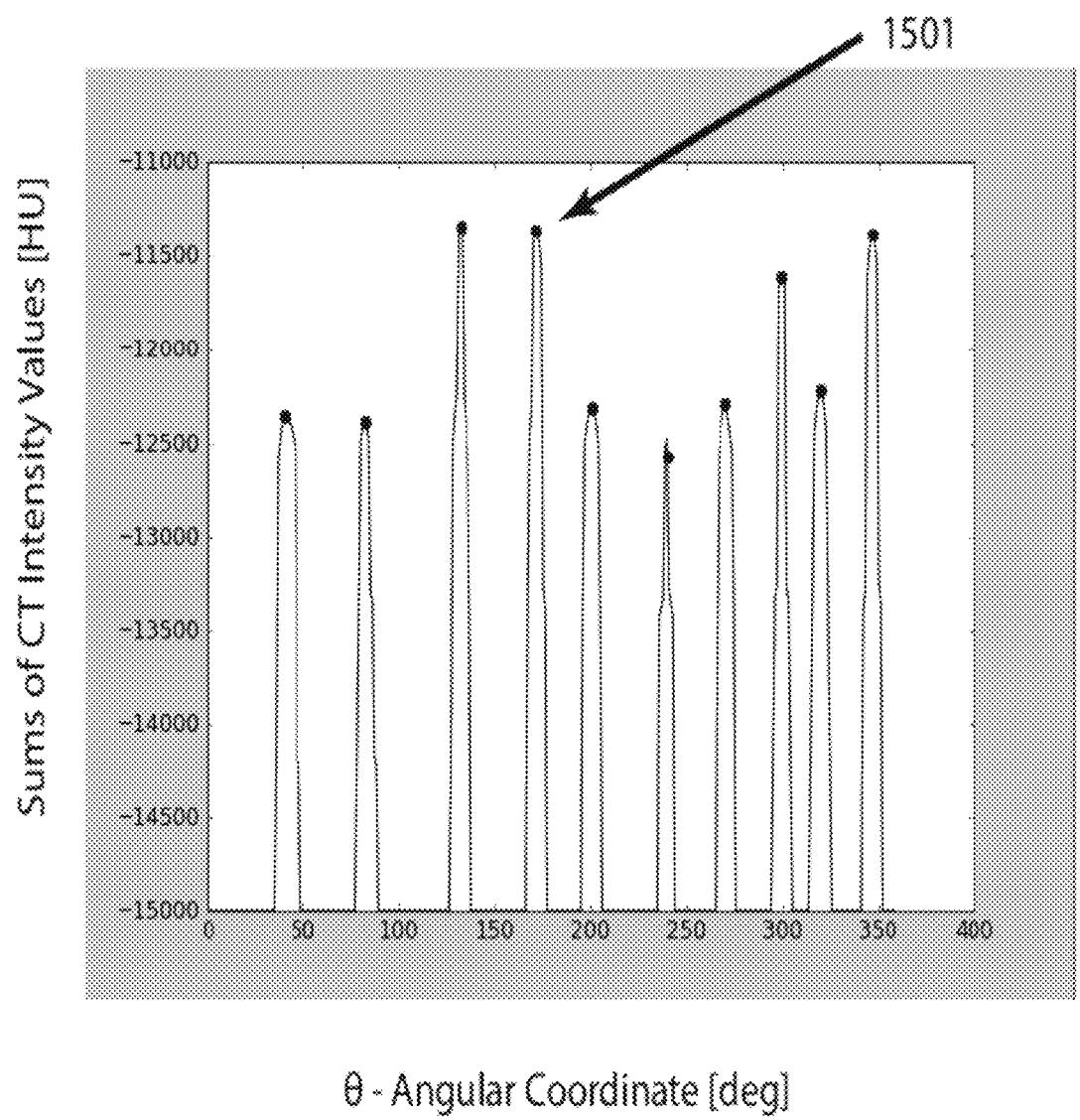
FIG. 15 depicts data values obtained by summing by rows the pixel intensities from FIG. 11.

The ordinate of the local maxima of the CT intensity sampled on the sampling cylinder, as in FIG. 11 represents the angle of each tine around the shaft of the electrode. FIG. 15 shows a plot of a vector of values obtained by summing by pixels rows the intensity values in the image of FIG. 11. The vector has been thresholded, setting to zero any values that fell below 50% of the maximum value found in the vector. The abscissa of the local maxima in this vector corresponds to the ordinate of the local maximain FIG. 11. The electrode identification algorithm identifies the local maxima in this vector, and determines in this way the angular coordinate of each single tine of the electrode.

Figure 16:
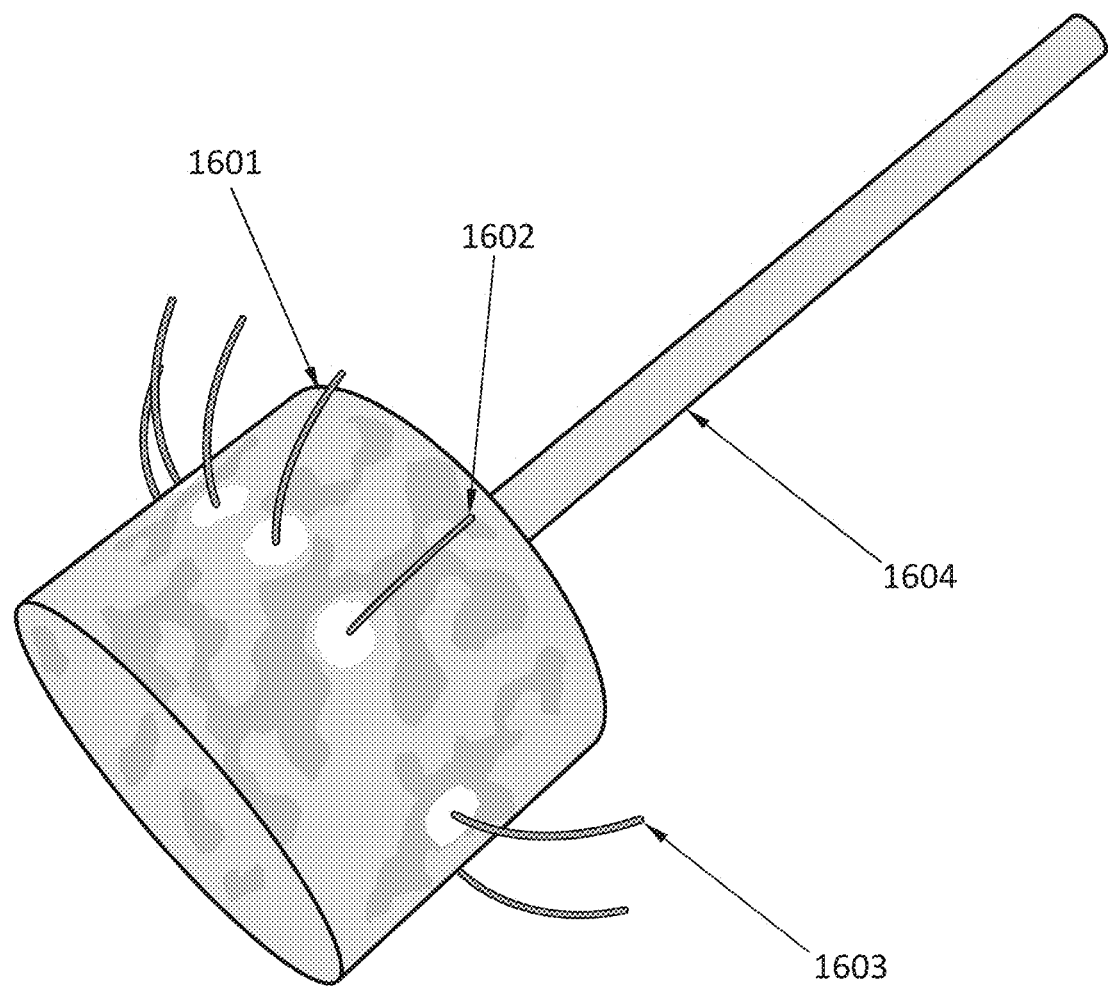
FIG. 16 depicts the sampling cylinder of FIG. 10 with the addition of an RFA electrode model to better illustrate the spatial relationship.

FIG. 16 illustrates the sampling cylinder of FIG. 10 where a computer model of and RFA electrode has been added to the rendering (1604). This electrode model has been built with tines matching the detected tine angles. As it is possible to appreciate, the tines of the model pass by the high intensity spots on the sampling cylinder, matching therefore the angular position of the tines of the true electrode as deployed in the tissues. This figure illustrates also the fact the angles between tines en be unevenly distributes. For instance the angle between tine (1603) and tine (1602) is greater than the angle between tine (1602) and tine (1601).

Figure 17:
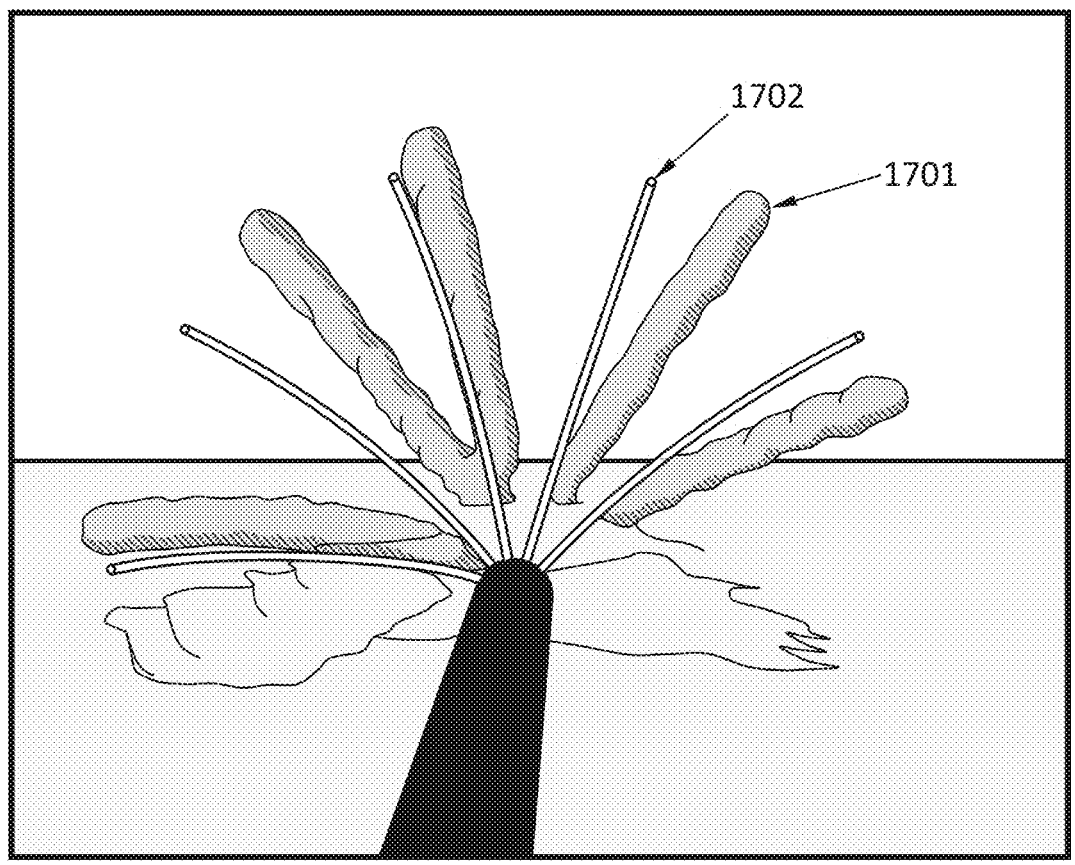
FIG. 17 depicts CT data thresholded to highlight the tines of an RFA electrode, and a computer model of an RFA electrode which has been built with a regular geometry of the tines.
Figure 18:
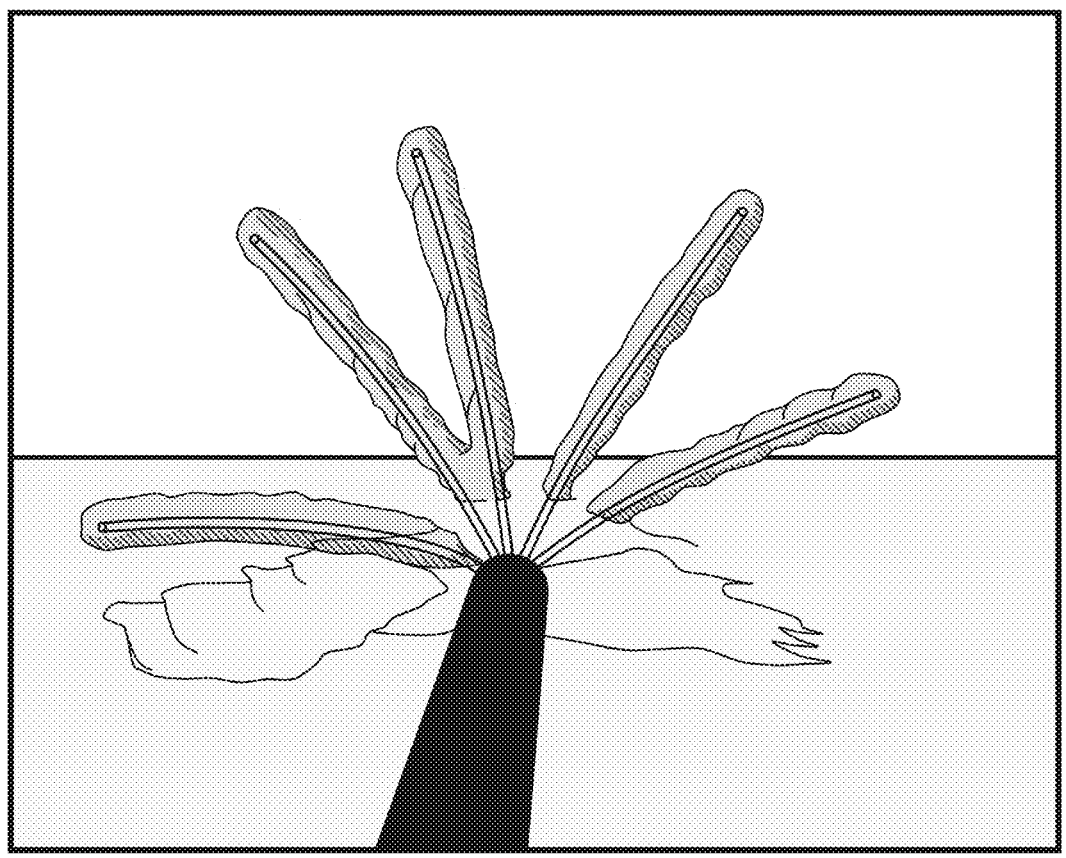
FIG. 18 depicts CT data thresholded to highlight the tines of an RFA electrode, and a computer model of an RFA electrode which has been built with a geometry of the tines matching the true geometry of the RFA electrode captured from the CT image.

FIGS. 17 and 18 further demonstrate the electrode identification algorithm. FIG. 17 shows a 2D slice of a CT 3D image intercepting the electrode shaft. The figure shows also thresholded values from the underlying 3D CT image (1701), where the threshold level was set to be high enough not to include tissues, but only the metallic probe tines, which have a high CT value. Superimposed to this image is the computer model of one RFA electrode, for which the position and orientation in the image have been determined with step 68 of the electrode identification algorithm, but where the angular distribution of the tines has been assumed to be regular. The specific electrode has 10 tines, and an angle between each two tines of 360/10=36 degrees was assumed. Clearly the model does not match the actual position of the tines in the tissues. The tines of the model (1702) do not align with tines in the CT image (1701).

FIG. 18 shows the same information, but the RFA electrode model has been updated to reflect the true angular position of the tines as identified by step 70 of the electrode identification algorithm. Clearly tines of the model match well the position of the true tines of the electrode as deployed in the tissues, and as captured by the CT image. The angles between any two tines are irregular. The updated electrode model can be used to estimate an ablation volume for the deployed electrode which is representative of the true geometry of the deployed electrode.

The electrode identification algorithm terminates at step 70, as the position and orientation of the electrode, and the angular position of each tine are recognized.

The above paragraphs have described an exemplar embodiment of an electrode identification algorithm part of the ablation device identification component (5). Previous paragraphs have also described the components that are part of the ablation system in FIG. 1 with the exception of the adequacy evaluation component (6).

The aim of adequacy evaluation component (6) is to highlight, with computer graphics, on a GUI, at any stage of a procedure, where one or multiple ablations are performed, which target tissues and margins have been treated and which not, in such a way that the adequacy can be evaluated in a visually and immediate manner.

The adequacy evaluation component (6) is best described following the flowchart of FIG. 2. In the next therefore the flowchart is illustrated and the adequacy evaluation component (6) is described.

At step 10 the operation of the ablation system starts and a suitable image of the patient is acquired. The image is fed to the tissue segmentation component (4) and defined as a reference image. The adequacy evaluation component (6) initializes a tissue damage map to have the same volume of the reference image and same spatial coordinates; the map is initialized to a status of no tissue damage.

The operator identifies/defines using the tissue segmentation component (4) the target tissues, and optionally target margins (step 12).

The operator optionally segments the local vasculature and optionally identifies/defines perfusion regions and perfusion values (step 14).

The operator uses common image guidance procedures to deploy the ablation device (1) at a desired intracorporeal location which is in operator's experience suitable to perform a first ablation. The operator, before activating the ablation device (1), acquires a confirmation image, which captures the position and orientation of the ablation device (1), and informs, though a GUI, the adequacy evaluation component (6) that a confirmation image is available (step 18).

The adequacy evaluation component (6) uses the device identification component (5) to recognize the positon and orientation of the ablation device (1), and optionally the geometry of the device as deployed in the tissues (step 20).

The adequacy evaluation component (6) uses device manufacturer data to estimate the ablation volume of the device. Optionally the adequacy evaluation component (6) can use computer models that simulate the physics of the ablation process, including the heat sink effect of the local vasculature, the effect of perfusion including the different perfusion rates for different tissues, and the actual geometry of the device as deployed in the tissues to estimate an ablation volume (step 22). FIG. 19 shows, as an example, a computational model, including an RFA electrode (1904), where a vessel (1901) is able absorb heat from an ablation site, as the temperature of blood is 37° C. and the temperature of the tissues at the ablation site exceeds 100° c. The presence of the vessels alters the temperature isodines, and shrinks the ablation volume, an effect known as "heat sink". Temperature isolines are represented as white stripes, where (1902) is the 60° C. isoline and (1903) the 100° C. isoline.

The adequacy evaluation component (6) will register the confirmation image to the reference image, allowing to refer the ablation device (1) position and orientation obtained from the device identification component (5) to the reference image. This will allow the adequacy evaluation component (6) to display, fused to the reference image, and to a representation of the target tissues, an estimated ablation volume The operator will assess the effects of the ablation, and in particular which portion of target tissues would be treated, and any possible damage to non-target tissues, from the visual representation of the ablation volume, of the reference image of the patient, and of the target tissues offered in a GUI by the adequacy evaluation component (6). If previous ablations have been run, because the operator has cycled on steps 40 to 16, the adequacy evaluation component (6) will also highlight which previous tissues have been treated, or which tissues are to be treated yet, or both (step 24).

If the position and orientation of the ablation device (1) are unsatisfactory the operator will re-position appropriately the ablation device (1) under image guidance and repeat steps 12 to 26 until the position and orientation of the ablation device (1) are satisfactory (step 26).

The operator, without moving the ablation device (1) from the position which was deemed to be satisfactory at step 26, will inform, through a GUI, the adequacy evaluation component (6) that the ablation is being started, and the operator will start the ablation by operating the ablation device controller (2) (step 28).

The adequacy evaluation component (6) will optionally start a communication with the ablation device controller (2) (e.g. via a serial port, via a USB connection, via a Ethernet connection, via wireless means, or via any other means of machine-to-machine communication) for gathering information characterizing the ablation process, such as the level and duration of ablative power being applied to the tissues, or information characterizing the status of tissues like impedance data in RFA, the electromagnetic reflection coefficient data in MWA, or temperature data (step 30).

Figure 22:
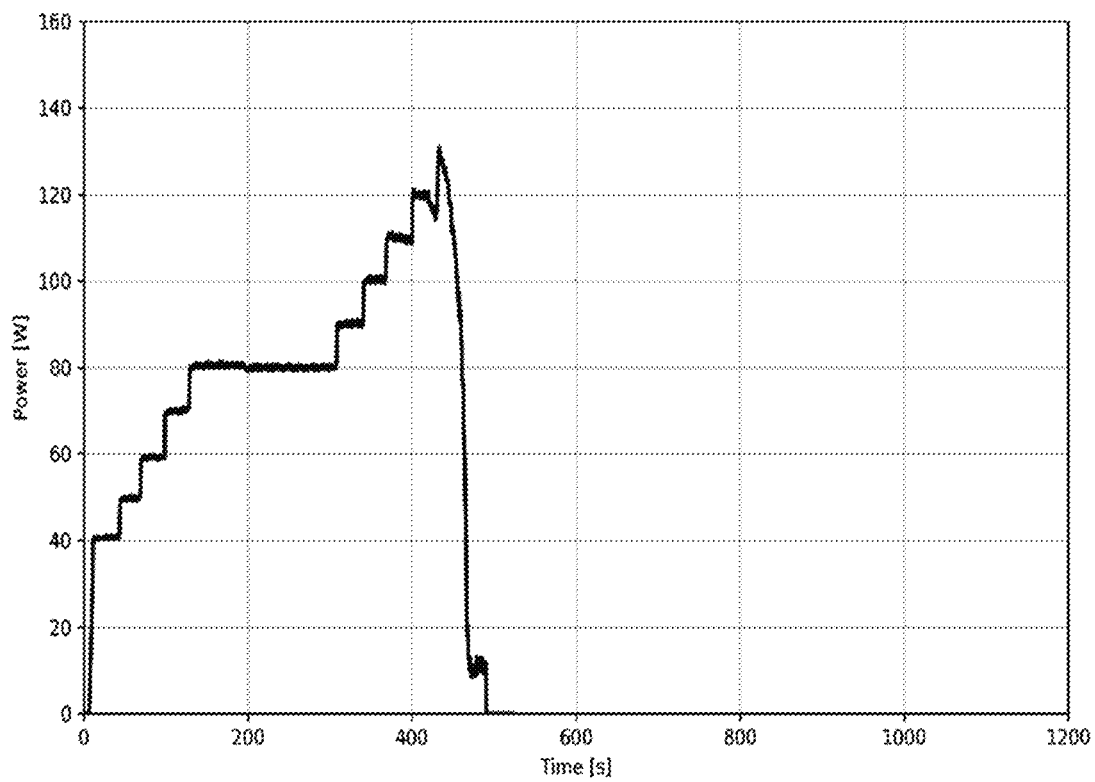
FIG. 22 depicts RF power information as collected from an RF power generator during an RF ablation.
Figure 23:
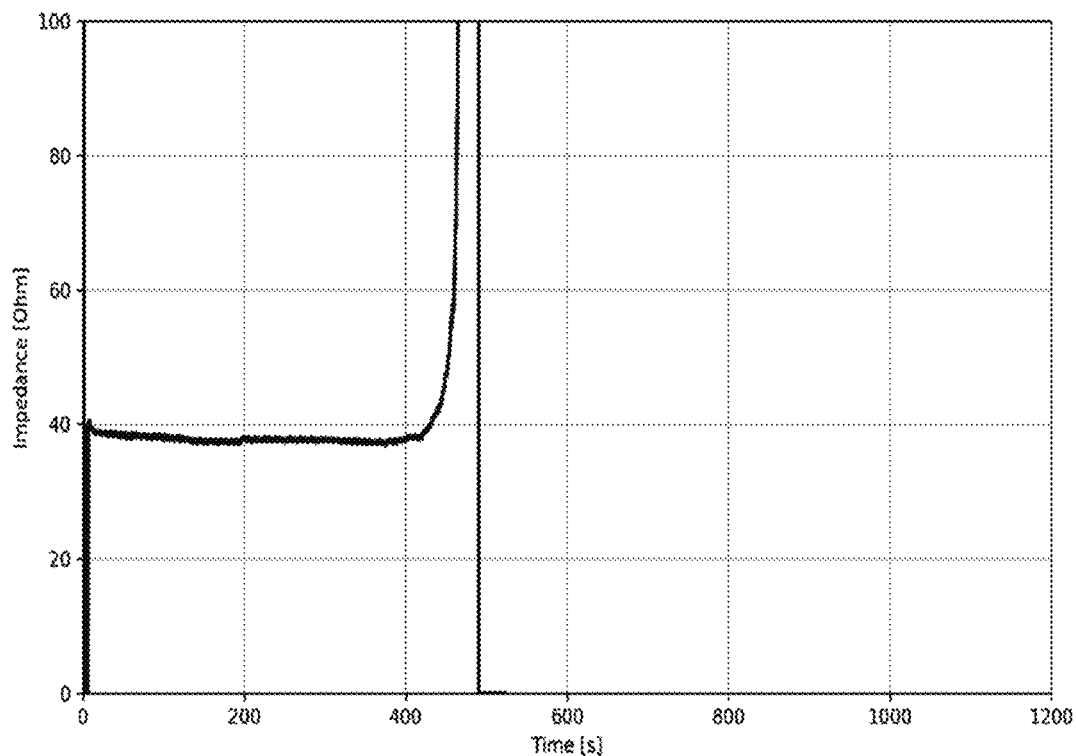
FIG. 23 depicts RF electrical impedance information as collected from an RF power generator during an RF ablation.

The data collected from the ablation device controller (2) during step 30 might be optionally used to update the estimated ablation volume, for example by using a computer model and re-computing the ablation volume based on the actual level of applied ablative power. FIG. 22 illustrates the temporal evolution of the applied power during an RFA ablation as collected by an RFA power generator (ablation device controller (2)). The power is varied over time by the operator according to a protocol specified by the manufacturer of the power generator and electrode. The actual delivered power depends, besides the variable settings of the operator, on the properties of the tissues, including the hydration state the perfusion rate. Retrieving data about the power applied from the ablation device controller (2), or other similar information that characterizes the ablation process in other forms of ablation, allows to run computer models based on this data and to obtain more accurate estimation of the ablation volume that has been procured in tissue. Ablation device controllers (2) optionally acquire data that characterizes the tissues. FIG. 23, for example, shows impedance data collected from an RFA power generator during the course of an ablation. Initially the impedance has a value of about 40 Ohms. Towards the end of the ablation the impedance raises quickly to more than 100 Ohms (and then decreases because the operator has switched off the power generator). The sharp increase in impedance reflects the fact that tissues have lost most of their water, which has evaporated under the intense heat of the ablation. Similar data, reflecting the status of tissues, can be used by computer models used to simulate ablation physics, to improve predictions in the estimate ablation volume. Models for thermal ablation for example estimate the water content of tissues during the ablation, and this data, or similar data can be used to estimate internal parameters of the model.

Upon termination of the ablation the operator informs the adequacy evaluation component (6), through a GUI, that the ablation has been terminated (step 34).

The adequacy evaluation component (6) uses the estimated ablation volume from step 22, or from step 32, if an update to the ablation volume was made, to mark treated tissues in the treated tissues map. The volume of tissues to be marked as treated is given from the ablation volume estimation steps 22 or 32. The spatial position and orientation of the estimated ablation volume are known form the device identification component (5) at step 20. This spatial information provided by the device identification component (5) is referred to the reference image and therefore to the treated tissues map, as the map by construction has the same system of spatial coordinates than the reference image.

The marking of tissues as treated is an accumulation process. If further ablations are performed, looping on steps 16 to 40, new tissues can be marked as treated, but a tissue that has been marked as treated cannot be unmarked.

Alternatively, when available, the adequacy evaluation component (6) might use further post-ablation images, registered to the reference image, to identify treated tissues and to mark them as treated in the treated tissues map.

The above operations complete step 36.

The treated tissues map, at this stage represents the volume of treated tissues from a first single ablation. If multiple ablations are performed looping on steps 16 to 40, the treated tissues map would have accumulated the volume of treated tissues for all the ablations that have been run.

The adequacy evaluation component (6) will display, using a GUI, the reference image defined in the tissue segmentation component (4), a representation of the target tissues, as defined in the tissue segmentation component (4), and representations that will allow the operator to estimate the adequacy. These representations, can, for example, highlight which target tissues have received treatment, or which target tissues still need treatment, or both, allowing a visual and straightforward evaluation of whether all target tissues have been treated, and therefore the evaluation of the adequacy of the procedure (step 38).

Figure 20:
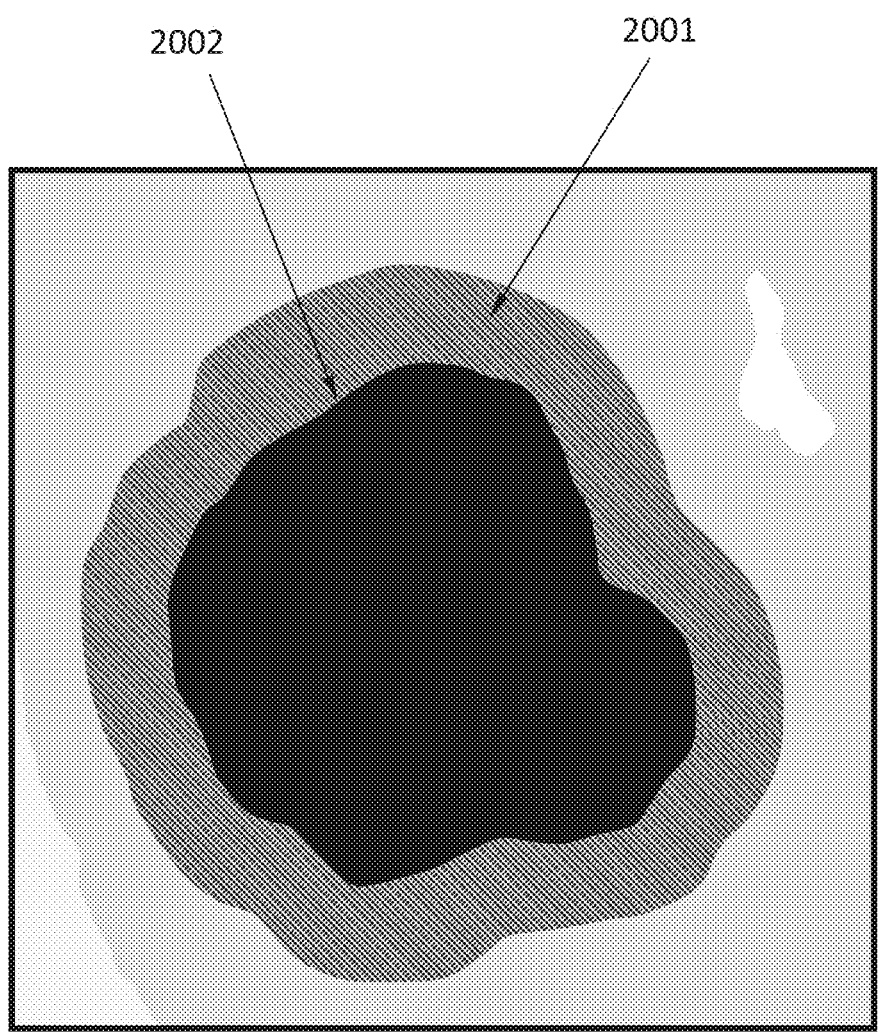
FIG. 20 depicts a CT slice and computer highlighted target tissues and margins.
Figure 21:
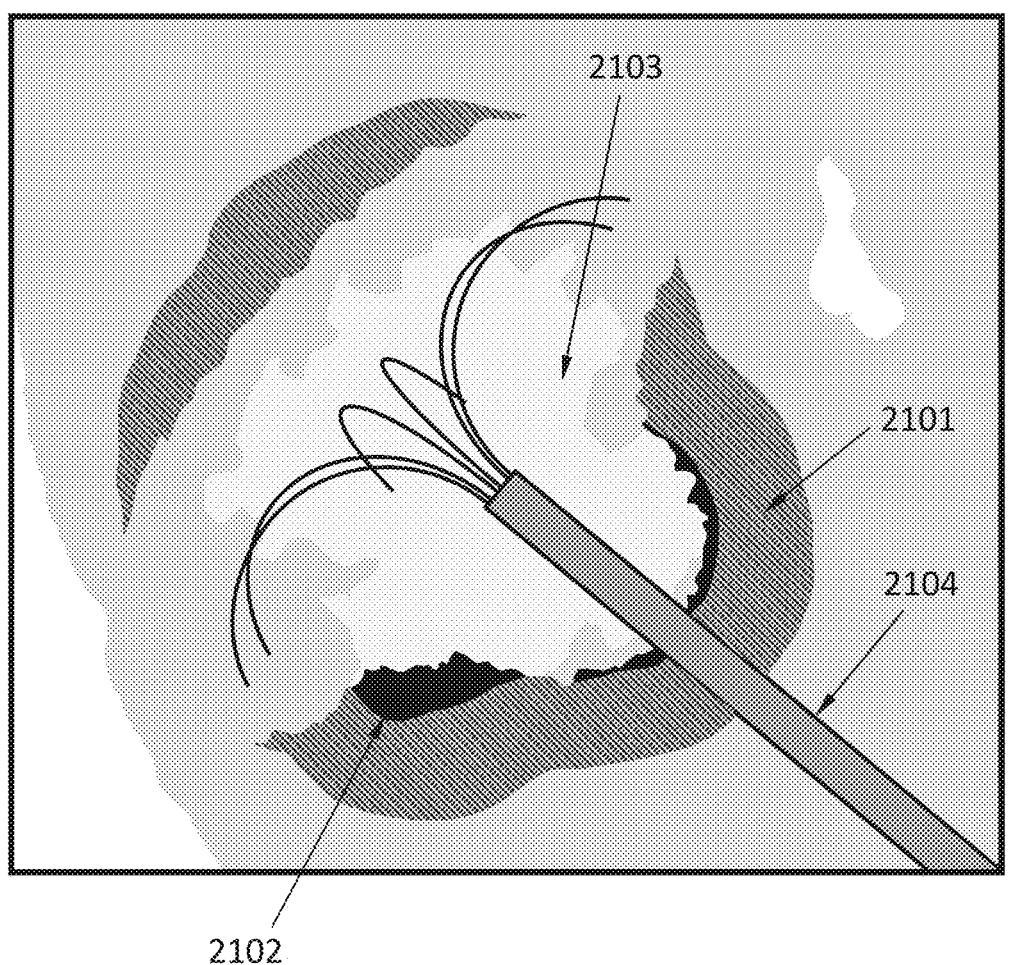
FIG. 21 depicts a CT slice with computer highlighted information that aids the evaluation of adequacy, namely a representation of target tissues and margins that still need treatment after a first ablation.

FIGS. 20 and 21 demonstrate the above step. FIG. 20 shows a 2D slice from the reference image, a segmented tumor (target tissues) and associated margins. The segmented tumor and margins are 3D volumes, of which a 2D slice in the same plane of the 2D slice of the reference image is represented. FIG. 21 shows a subtraction view, where the volume of treated tissues has been subtracted from the volume of the target tissue and margins. A 2D slice through these volumes and through the reference image is represented. The subtraction representation highlights therefore the tissues that still need treatment, and makes the evaluation of adequacy a visual and straightforward task.

The above operations complete step 38.

If adequacy has been reached at step 40 the procedure is terminated.

If the adequacy has not been achieved the operator will loop through steps 16 to 40 until adequacy is reached.

What is claimed is:

1. A system for ablation treatment of tissues comprising:
at least one tissue ablation device for treating tissue with ablation comprising one of:
an RF ablation electrode working in monopolar fashion;
multiple RF ablation electrodes working in multipolar fashion;
a microwave ablation antenna;
a cryoablation probe; and
one or more irreversible electroporation electrodes working together;
an ablation device controller for controlling ablative operation of the at least one ablation device, the ablation device controller configured to supply at least one of an adjustment of energy and a temperature to the ablation device;
an imaging component for capturing one or more images of tissues designated for treatment using the at least one ablation device, wherein:
the captured images include the actual position and orientation of the at least one ablation device deployed in the designated tissues; and
the imaging component is selected from a group consisting of a CT scanner, a US scanner, an MRI scanner, a FL system;
a display comprising a GUI configured to receive an operator instruction selecting a reference image from the one or more images captured by the imaging component, and select the reference image based on the user instruction, and wherein the GUI is used to define target tissues for ablative treatment on the selected reference image based on a user instruction defining the target tissues;
an ablation device identification component configured to:
identify the actual position and orientation of the at least one ablation device, as deployed, on at least one confirmation image captured with the imaging component, the at least one confirmation image being different from the reference image, wherein identifying further comprises:
receiving operator inputs, wherein the operator inputs include at least a first input selecting the at least one confirmation image, a second input identifying a point at a distal end of an image of the probe in the at least one confirmation image, and a third input identifying a point at a proximal end of the image of the probe in the at least one confirmation image; and
identify the actual position and orientation of the at least one ablation device as a function of the operator inputs; and
register the identified actual position and orientation relative to the confirmation; and
provide a representation of the identified actual position and orientation of the at least one ablation device on the reference image relative to the target tissues using the registered actual position and orientation;
an adequacy evaluation component comprising a visual map of predicted treated tissues superimposed on the GUI relative to the reference image defined in the tissue segmentation component, said map identifying, using computer graphics superimposed on the reference image, a first portion of the target tissues that are predicted to be treated by operation of the at least one ablation device in its identified actual position and orientation, and a second portion of the target tissues that are predicted to have not been treated by operation of the at least one ablation device in its identified actual position and orientation, said first and second portions being identified in relation to the defined target tissues for treatment, wherein the adequacy evaluation component is configured to update the estimated ablation volume for a simulated ablative operation based on the identified actual position and orientation of the at least one ablation device;
wherein the map of predicted treated tissues is built by accumulating an estimated ablation volume comprising a simulated ablative operation using the identified actual position and orientation information of the at least one ablation device provided by the ablation device identification component.

2. The system according to claim 1, wherein the adequacy evaluation component is programmed with manufacturer operational data for the at least one ablation device for estimating the volume and geometry of an ablation using the at least one ablation device.

3. The system according to claim 1, wherein the adequacy evaluation component, for the actual position and orientation of the at least one ablation device, as deployed in the defined target tissues for treatment, displays on the GUI, before the activation of the at least one ablation device, an estimated ablation volume to the reference image and to the map of the predicted treated tissues, allowing a visual assessment of which new tissues would be treated by activating the ablation device at the actual position and orientation of the at least one ablation device, as deployed.

4. A method for ablation therapy of tissue, the method comprising:
(a) capturing images of tissues designated for treatment by ablation with an imaging component, and defining one of the captured images as a reference image;
(b) using a GUI to segment tissues from the reference image and define said segmented tissues as target tissues for treatment by ablation;
(c) positioning an ablation device in the tissues designated for treatment;
(d) capturing, using the imaging component and before activating the ablation device, a confirmation image identifying the actual position and orientation of the ablation device as deployed in the tissues designated for treatment, wherein identifying further comprises:
receiving operator inputs, wherein the operator inputs include at least a first input selecting the at least one confirmation image, a second input identifying a point at a distal end of an image of the probe in the at least one confirmation image, and a third input identifying a point at a proximal end of the image of the probe in the at least one confirmation image; and
identifying the actual position and orientation of the at least one ablation device as a function of the operator inputs;
(e) estimating the ablation volume of the ablation device, using a computer, before activating the ablation device, for a simulated ablative operation based on the identified actual position and orientation of the ablation device;
(f) displaying on a display in operative communication with the GUI the reference image with graphical representations of the actual position and orientation of the ablation device, as identified from the confirmation image, the estimated ablation volume, and a predicted treated tissues map superimposed on the reference image, said predicted treated tissues map comprising a first portion of the target tissues that are predicted to be treated by operation of the ablation device in its identified actual position and orientation, and a second portion of the target tissues that are predicted to have not been treated by operation of the ablation device in its identified actual position and orientation, said first and second portions being identified in relation to the defined target tissues for treatment;
(g) starting an ablation treatment by activating the ablation device using an ablation device controller in operative communication with said ablation device; and
(h) repeating steps (c) to (g) by repositioning and operating the ablation device until the target tissues have been treated.

5. The method of claim 4, further including:
segmenting, using the GUI, the vasculature of the tissues designated for treatment on the reference image; and
accounting for its heat sink effect when estimating the ablation volume for a simulated ablative operation based on the identified actual position and orientation information of the ablation device.

6. The method of claim 4, further including:
segmenting, using the GUI, one or more regions of the tissues designated for treatment on the reference image and assigning perfusion rates for each of the one or more regions; and
accounting for the effect of said assigned perfusion rates when estimating the ablation volume for a simulated ablative operation based on the identified actual position and orientation information of the ablation device.

7. The method of claim 4, further including:
using images captured with the imaging component to identify one or more regions of the tissues designated for treatment and estimating perfusion rates for each of the one or more regions; and
accounting for the effect of said perfusion rates when estimating the ablation volume for a simulated ablative operation based on the identified actual position and orientation information of the ablation device.

8. The method of claim 4, further including:
using images captured with the imaging component to identify the geometry of the ablation device as deployed in the tissues designated for treatment and
using the identified geometry of the ablation device, as deployed, when estimating the ablation volume for a simulated ablative operation based on the identified actual position and orientation information of the ablative device.

9. The method of claim 4, further including:
receiving data from the ablation device controller regarding at least one of the ablative operation of the ablation device and the real-time status of the target tissues designated for treatment; and
accounting for the received data when estimating the ablation volume for a simulated ablative operation based on the identified actual position and orientation information of the ablation device.

10. The method of claim 9, wherein the received data regarding the ablative operation of the ablation device relates to the power delivered from the ablation device when activated.

11. The method of claim 9, wherein the received data regarding the real-time status of the target tissues designated for treatment relates to at least one of the electrical impedance of target tissues, the electrometric reflection coefficient of target tissues, and the temperature of target tissues.

12. The method of claim 9, further including:
using estimated ablation volume, and the position and orientation of the ablation device, to mark, using the GUI, on an actual treated tissues map on the display a portion of the tissues designated for treatment that have been treated by the ablation device; wherein the actual treated tissues map, initialized to a status of no tissues treated, can be progressively updated to update said portion of the tissues designated for treatment as additional ablations are run after the ablation device has been moved to a new position and orientation in accordance with step h; and displaying on the display at least the reference image, the target tissues designated for treatment, and graphical indications superimposed on the reference image identifying which portions of the target tissues have been treated and which portions of the target tissues have not been treated.

13. The system according to claim 1, wherein said ablation device controller is capable of collecting data relating to tissue treated with ablation from the at least one ablation device, wherein said data relating to tissue treated with ablation comprises at least one of an electrical impedance, an electromagnetic reflection coefficient, and a temperature of said treated tissue.

14. The method of claim 4, further including:
providing an indication on the display that the ablation treatment has started, when the ablation device has been activated; and
providing an indication on the display then that the ablation treatment has terminated, when the ablation device has been deactivated.

\* \* \* \* \*

UNITED STATES PATENT AND TRADEMARK OFFICE
CERTIFICATE OF CORRECTION

PATENT NO. : 11,419,660 B2
APPLICATION NO. : 15/427884
DATED : August 23, 2022
INVENTOR(S) : Andrea Borsic Page 1 of 1

It is certified that error appears in the above-identified patent and that said Letters Patent is hereby corrected as shown below:

In the Specification

At Column 1, Lines 12-15, under the section entitled STATEMENT REGARDING FEDERALLY SPONSORED RESEARCH OR DEVELOPMENT, the text should be deleted and replaced with the following: "This invention was made with government support under R43 CA189515 awarded by the National Institutes of Health. The government has certain rights in the invention."

Signed and Sealed this
Twenty-sixth Day of September, 2023

Katherine Kelly Vidal
*Director of the United States Patent and Trademark Office*